(12) United States Patent
Zhang et al.

(10) Patent No.: US 10,240,150 B2
(45) Date of Patent: *Mar. 26, 2019

(54) AVIAN INFLUENZA VIRUS MIRNA, AND APPRAISAL, DETECTION, AND APPLICATION THEREOF

(71) Applicant: JIANGSU MICROMEDMARK BIOTECH CO., LTD., Jiangsu (CN)

(72) Inventors: Chenyu Zhang, Beijing (CN); Ke Zeng, Beijing (CN); Jin Wang, Beijing (CN); Xihan Li, Beijing (CN)

(73) Assignee: JIANGSU MICROMEDMARK BIOTECH CO., LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,132

(22) PCT Filed: Dec. 9, 2014

(86) PCT No.: PCT/CN2014/093384
§ 371 (c)(1),
(2) Date: Jun. 9, 2016

(87) PCT Pub. No.: WO2015/085904
PCT Pub. Date: Jun. 18, 2015

(65) Prior Publication Data
US 2017/0022496 A1    Jan. 26, 2017

(30) Foreign Application Priority Data
Dec. 9, 2013  (CN) .......................... 2013 1 0664639

(51) Int. Cl.
*C12N 15/113*  (2010.01)
*C12Q 1/70*    (2006.01)
*G01N 33/569*  (2006.01)

(52) U.S. Cl.
CPC ............ *C12N 15/113* (2013.01); *C12Q 1/701* (2013.01); *C12N 2310/141* (2013.01); *C12Q 2600/136* (2013.01); *C12Q 2600/158* (2013.01); *C12Q 2600/178* (2013.01); *G01N 33/56983* (2013.01); *G01N 2333/11* (2013.01)

(58) Field of Classification Search
None
See application file for complete search history.

(56) References Cited

U.S. PATENT DOCUMENTS

| 2008/0045472 A1 | 2/2008 | Brahmachari et al. |
| 2010/0016414 A1 | 1/2010 | Brahmachari et al. |

FOREIGN PATENT DOCUMENTS

WO    WO/2010/101663 A2    9/2010

OTHER PUBLICATIONS

Lau, et al. (2006) Science v.313, No. 5785.*
Subbarao, et al. (1998) "Characterization of an Avian Influenza A (H5N1) Virus Isolated from a Child with a Fatal Respiratory Illness." Science, v.279:393-6.*
Guan, Y., et al.; Influenza A VirusSegment4 . . . ; Genbank AY059482; Mar. 23, 2012.
Shen, Yansen; Relationship of Gene Silencing . . . ; China Doctoral Dissertations; Apr. 28, 2012.
Rogers, James, et al; Preliminary MicroRNA Analysis in Lung Tissue . . . ; Viral Immunology, vol. 25, # 1; Dec. 31, 2012.

* cited by examiner

*Primary Examiner* — Jennifer Pitrak McDonald
(74) *Attorney, Agent, or Firm* — Smith, Gambrell & Russell, LLP.

(57) ABSTRACT

The present invention relates to an avian influenza virus miRNA and the identification, detection and application thereof. In particular, a kind of specific microRNA, miR-HA-3p, is screened for the first time through detecting the microRNA expression levels in samples of animals with avian influenza. The experiments prove that the miR-HA-3p, as a microRNA marker, can be very effective in detecting avian influenza virus and avian influenza. Furthermore, inhibiting the function of miR-HA-3p can be very effective in relieving symptoms of avian influenza and treating avian influenza. The microRNA revealed in the present invention for the first time can be developed into a detection agent and a therapeutic agent as well as the corresponding kits for the detection and treatment of avian influenza (e.g., H5N1).

4 Claims, 20 Drawing Sheets
Specification includes a Sequence Listing.

A miR-H5N1-HA (SEQ ID No: 5)

```
          C U G                  AG                       A A GAGAA A
CCUUGCUA     GGCUC    AAAUAGUCCUCU                          A
GGGACGAU   UCGAG   UUUAUCAGGAGA                            AGA
         A       G              A A A AGAA                A
``` miR-H5N1-PA-1 (SEQ ID No: 6)

```
                                                              GAAC
AAGUC UGUUUCA UGUAUUCGGAUUUCC AC U UUAUUGAU              G
UUUAG ACAAAGU ACGUAAGCCUAGCGG  UG  AAUAACUA            AGCG G
     C C    U AU              C C AAG    G AC         A
``` miR-H5N1-PA-2 (SEQ ID No: 7)

```
       C U G             AG                    A A A AGC
UUAUCAAG   GAUCCAG   CGAAU UCAA                   A
AGUAGUUC   UUAGGUU  GCUUA AGUU                  AGCG U
        A AG      GA     G AC   A                C
```

A (SEQ ID No: 10)

SEQUENCE LISTING

```
<160> NUMBER OF SEQ ID NOS: 10

<210> SEQ ID NO 1
<211> LENGTH: 22
<212> TYPE: RNA
<213> ORGANISM: Avian influenza virus H5N1

<400> SEQUENCE: 1
aggacuauuu ggagcuauag ca                                           22

<210> SEQ ID NO 2
<211> LENGTH: 22
<212> TYPE: RNA
<213> ORGANISM: Avian influenza virus H5N1

<400> SEQUENCE: 2
ggacuauuug gagcuauagc ag                                           22

<210> SEQ ID NO 3
<211> LENGTH: 22
<212> TYPE: RNA
<213> ORGANISM: Avian influenza virus H5N1

<400> SEQUENCE: 3
gaggacuauu uggagcuaua gc                                           22

<210> SEQ ID NO 4
<211> LENGTH: 20
<212> TYPE: RNA
<213> ORGANISM: Avian influenza virus H5N1

<400> SEQUENCE: 4
ggacuauuug gagcuauagc                                              20

<210> SEQ ID NO 5
<211> LENGTH: 76
<212> TYPE: RNA
<213> ORGANISM: Avian influenza virus H5N1

<400> SEQUENCE: 5
```

```
ccuugcuacu gggcucagaa auaguccucu aagagaaaga agaagaaaaa gaggacuauu    60
uggagcuaua gcaggg                                                   76

<210> SEQ ID NO 6
<211> LENGTH: 101
<212> TYPE: RNA
<213> ORGANISM: Avian influenza virus H5N1

<400> SEQUENCE: 6
aagucuguuu cauguauucg gauuccacu uuauugauga acgaggcgaa ucaauaauug    60
uagaaccugg cgauccgaau gcauuauga aacaccgauu u                        101

<210> SEQ ID NO 7
<211> LENGTH: 74
<212> TYPE: RNA
<213> ORGANISM: Avian influenza virus H5N1

<400> SEQUENCE: 7
uuaucaagcu ggauccagag cgaauucaac aaagcaugcg aauugacaga uucgaguugg    60
auugaacuug auga                                                    74

<210> SEQ ID NO 8
<211> LENGTH: 23
<212> TYPE: RNA
<213> ORGANISM: Homo sapiens

<400> SEQUENCE: 8
aguaacuuca uuuauagucc ucc                                          23

<210> SEQ ID NO 9
<211> LENGTH: 24
<212> TYPE: RNA
<213> ORGANISM: Mus musculus

<400> SEQUENCE: 9
uuuauagcuc uaggguagua cucg                                         24

<210> SEQ ID NO 10
<211> LENGTH: 76
<212> TYPE: RNA
<213> ORGANISM: artificial sequence
<220> FEATURE:
<223> OTHER INFORMATION: precursor miRNA

<400> SEQUENCE: 10
ccuugcuacu gggcucagaa auaguccucu aagagaaaga agaagaaaaa gaggacuauu    60
uggagcuaua gcaggg                                                   76
```

AVIAN INFLUENZA VIRUS MIRNA, AND APPRAISAL, DETECTION, AND APPLICATION THEREOF

TECHNICAL FIELD

The present invention pertains to the biological and medical field, in particular to avian influenza virus miRNAs and the identification, detection and application thereof.

BACKGROUND ART

Influenza virus particles are covered by two types of surface glycoproteins, one is phytohemagglutinin (i.e., H), and the other is neuraminidase (i.e., N). Type H is divided into 15 subtypes, and type N is divided into 9 subtypes.

All human avian influenza viruses can cause avian influenza, but not all of the avian influenza viruses can cause human influenza. In the avian influenza viruses, H5, H7 and H9 can infect human, in which H5 is highly pathogenic, and H5N1 is a subtype of avian influenza virus. H5N1 is newly added to the list of infectious diseases, the occurrence of which, as stipulated by the regulations in the Infectious Disease Prevention Act from the Ministry of Public Health, must be reported, also known as highly pathogenic human avian influenza. Basing on their pathogenicity, avian influenza can be divided into highly pathogenic and low pathogenic avian influenza, and H5N1 belongs to the highly pathogenic avian influenza viruses.

In 1997, the H5N1 virus was isolated and identified for the first time from an influenza death case sample of a 3-year-old child in Hong Kong, China. By 2012, most of the human cases of infection have been directly from birds, only individual cases have been considered being from infected persons, and it is generally believed that the H5N1 virus has not been able to establish a sustained human-to-human transmission chain. Patients with severe avian influenza are generally infected with the subtype H5N1 virus. The patients show acute onset, and their early-stage performance is similar to that of common influenza, mainly including fever, with the body temperature being constantly above 39° C. and the course being 1-7 days, usually 3-4 days, accompanied by symptoms like runny nose, nasal congestion, cough, sore throat, headache, muscle aches and general discomfort. Some patients may have nausea, abdominal pain, diarrhea, watery stools and other digestive tract symptoms. Critical patients experience rapid development of the disease, which may lead to pneumonia, acute respiratory distress syndrome, pulmonary haemorrhage, pleural effusion, pancytopenia, renal failure, sepsis, shock and other complications. The total number of leukocytes is generally not increased, or even lowered. The critical patients generally have decreased total number of leukocytes and lymphocytes, accompanied with thrombocytopenia.

H5N1 subtype avian influenza virus is a type of virus that has the strongest infectivity and the highest lethality and is most prevalent in the avian influenza viruses found so far, which has been epidemic in many countries of the world.

Presently there is no effective and specific therapies for this disease, and vaccination is an effective preventive measure and key link. Therefore, the development of a safe, efficient vaccine with low-cost becomes one of the current hotspots of avian influenza prevention and control, and the vaccine development has made a lot of research achievements. However, since the virus mutates fast and has a variety of variants, the research and development speed cannot guarantee the effective resistance against viral variants; therefore, further researches on H5N1 invasion process and development of new therapies are more pressing tasks.

Micro ribonucleic acids (microRNA, or miRNA for short) are a class of non-coding, single stranded, small ribonucleic acid molecules with 19-23 nucleotides in length. They are highly conserved in evolution, and widely present in cells. Micro ribonucleic acids inhibit the translation of target mRNAs by recognizing an non-translated sequence at the 3' end of the target mRNA and complementing not completely thereto. Owing to the diversity of the sequence, structure, abundance and expression, the micro ribonucleic acid becomes a powerful regulator for messenger RNAs and plays an unimaginably important role in the field of gene expression regulation.

Micro ribonucleic acids are closely related to many normal physiological activities of animals, involving in development, tissue differentiation, apoptosis, energy metabolism and other aspects of life activities of biological individuals. Moreover, micro ribonucleic acids are also inextricably linked with the occurrence and development of many diseases, and when a certain disease occurs, the expression of some micro ribonucleic acids are always up-regulated, and some are down-regulated.

Relevant studies have shown that, after infecting host cells, viruses or microorganisms will encode specific miRNAs that act on the host immune-related mRNAs to regulate the host cytokine system of the host and further affect the immune regulation.

In summary, in order to prevent and treat avian influenza more effectively, there is an urgent need to develop relevant reagents and methods for the detection and treatment of avian influenza.

Contents of the Invention

The object of the present invention is to provide relevant reagents and methods for effective detecting and treating of avian influenza.

In the first aspect of the present invention, provided is an isolated miRNA selected from:

(i) miRNA with a sequence as shown in SEQ ID NO: 1, 2 or 3, or (ii) miRNA with a length of 20-26 nt and a core sequence as shown in SEQ ID NO.: 4; or (iii) miRNA complementary to the said nucleotide sequence of miRNA in (i) or (ii).

In another preferred example, said "complementary" includes "substantially complementary" (the number of non-complementary bases ≤3, preferably ≤3, more preferably ≤1) and "fully complementary".

In another preferred example, said miRNA is from avian influenza virus.

In another preferred example, said miRNA is from avian influenza virus H5N1.

In another preferred example, said miRNA is isolated from blood, body fluids or tissue samples of human or non-human mammals.

In another preferred example, said blood is plasma and/or serum.

In another preferred example, said non-human mammals are mice, rats, rabbits, pigs, bovine, sheep, etc.

In another preferred example, said miRNA is isolated from human.

In the first aspect of the present invention, provided is an isolated or artificially constructed precursor miRNA which can be cut and expressed as the miRNA of the first aspect of the present invention in animal cells.

In another preferred example, said animal cells include human cells.

In the third aspect of the present invention, provided is an isolated polynucleotide which can be transcribed in an animal cell into a precursor miRNA which can be cut and expressed into the miRNA as said in the first aspect of the present invention.

In another preferred example, said polynucleotide has the structure of formula I:

$$Seq_{forward}\text{-}X\text{-}Seq_{reverse} \qquad \text{Formula I}$$

In the formula I, $Seq_{forward}$ is a nucleotide sequence that can be expressed as said miRNA in an animal cell;

$Seq_{reverse}$ is a nucleotide sequence substantially complementary or fully complementary to $Seq_{forward}$;

X is a spacer sequence between $Seq_{forward}$ and $Seq_{reverse}$, and said spacer sequence is not complementary to $Seq_{forward}$ and $Seq_{reverse}$;

and after being transferred into the human cell, the structure shown in the formula I forms a secondary structure shown in formula II:

$$\text{Formula II}$$

$$Seq_{forward} \frown$$
$$\quad || \quad X,$$
$$Seq_{reverse} \smile$$

In the formula II, $Seq_{forward}$, $Seq_{reverse}$ and X are defined above, and || indicates the complementary base pairing relationship between $Seq_{forward}$ and $Seq_{reverse}$.

In the fourth aspect of the present invention, provided is a vector comprising the miRNA of the first aspect, or the polynucleotide of the second aspect of the present invention.

In the fifth aspect of the present invention, provided is use of the miRNA of the first aspect of the present invention for: (a) the preparation of a reagent, a detecting chip or a kit for the detection of avian influenza; (b) the preparation of a regulator for regulating the PCBP2 expression or activity; and (c) the preparation of reagents for regulating the expression of cytokines.

In another preferred example, said regulator for regulating PCBP2 expression or activity is an inhibitor for down-regulating the PCBP2 expression or activity.

In another preferred example, said cytokines include TNFα, IFN-β, IL-6, IL-1β, or a combination thereof.

In the sixth aspect of the present invention, provided is a nucleic acid chip (e.g., a miRNA chip), comprising:

a solid-phase carrier; and oligonucleotide probes orderly fixed on said solid-phase carrier, said oligonucleotide probes specifically capturing the miRNA of the first aspect of the present invention.

In the seventh aspect of the present invention, provided is use of the nucleic acid chip of the sixth aspect of the present invention for the preparation of a kit for the detection of avian influenza.

In the eighth aspect of the present invention, provided is a kit comprising the nucleic acid chip of the seventh aspect or the miRNA of the first aspect of the present invention.

In the ninth aspect of the present invention, provided is an inhibitor specifically inhibiting or blocking the miRNA of the first aspect of the present invention.

In another preferred example, said inhibitor is a miRNA sponge, or an antisense nucleic acid or a small molecule compound complementary to the miRNA sequence.

In another preferred example, said inhibitor is a nucleic acid (e.g., RNA, DNA or the like) complementary to the nucleotide sequence of the miRNA of (i) or (ii).

In the tenth aspect of the present invention, provided is use of the inhibitor for said miRNA of the ninth aspect of the present invention for the preparation of (a) a medicament for treating avian influenza, (b) a medicament for relieving the symptoms of avian influenza, (c) a medicament for reducing the quantity of avian influenza virus in a host animal, (d) a medicament for reducing the death rate of avian influenza, and (e) a medicament for reducing overactive immune responses.

In the eleventh aspect of the present invention, provided is a pharmaceutical composition comprising a pharmaceutically acceptable carrier and an inhibitor for specifically inhibiting or blocking the miRNA of the first aspect of the present invention.

In another preferred example, said miRNA inhibitor comprises a miRNA sponge, and an antisense nucleic acid complementary to the sequence of miRNA.

In the twelfth aspect of the present invention, provided is a method for screening medicament candidates for treating avian influenza, comprising the steps of:

(a) providing a test group and a control group, wherein to the said test group, a candidate substance is applied to cells or animals of the test group, and the expression level of miR-HA-3p in said test group is detected after the application, and in said control group, the same conditions as the test group are applied, without applying the candidate substance to cells or animals of the control group; and (b) comparing the expression level of miR-HA-3p in the test group with that in the control group;

wherein if the expression level of miR-HA-3p in the test group is significantly lower than that in the control group, it is indicated that this candidate substance is a medicament candidate for treating avian influenza.

In another preferred example, the sequence of said miR-HA-3p is as shown in SEQ ID NOs: 1-3.

In another preferred example, said animals include mice, and said cells include cells cultured in vitro.

In the thirteenth aspect of the present invention, provided is a use of miR-HA-3p for the preparation of a regulator or a pharmaceutical composition for down-regulating the PCBP2 expression or activity.

In another preferred example, the sequence of said miR-HA-3p is as shown in SEQ ID NOs: 1-3.

It should be understood that all of the various technical features described above and specifically described hereinafter (such as examples) can be combined with one another within the scope of the present invention, so as to form new or preferred technical solutions. Due to space limitations, these are no longer tired out one by one.

DESCRIPTION OF DRAWINGS

FIG. 8 shows the research results of the lung tissues of multiple groups of laboratory mice by histopathological method.

Figure 1:
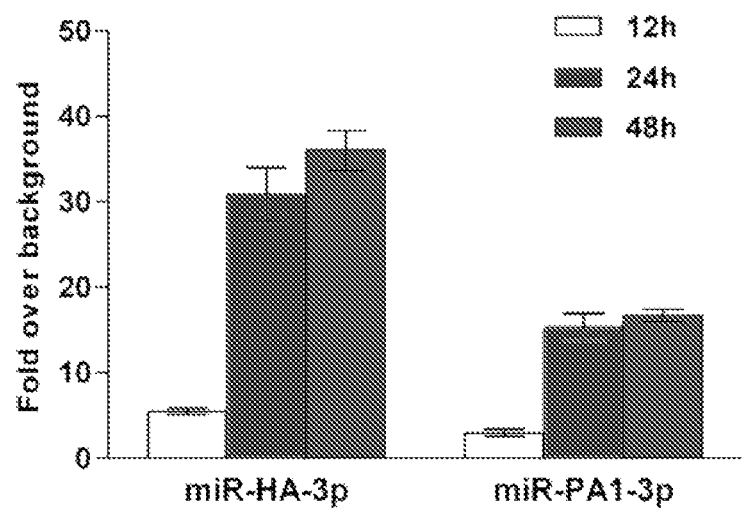
FIG. 1 shows that the avian influenza H5N1 will release a special small molecule miR-HA-3p after infecting a host cell.
Figure 1:
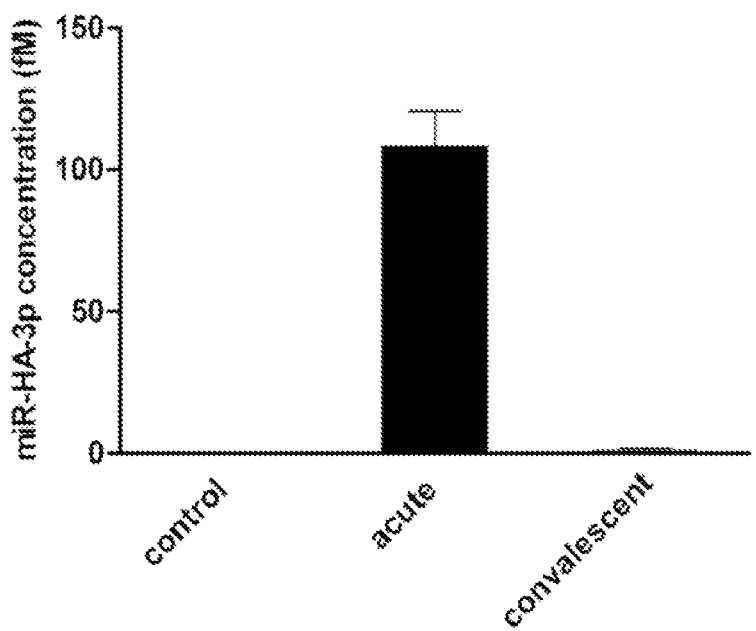
Figure 1:
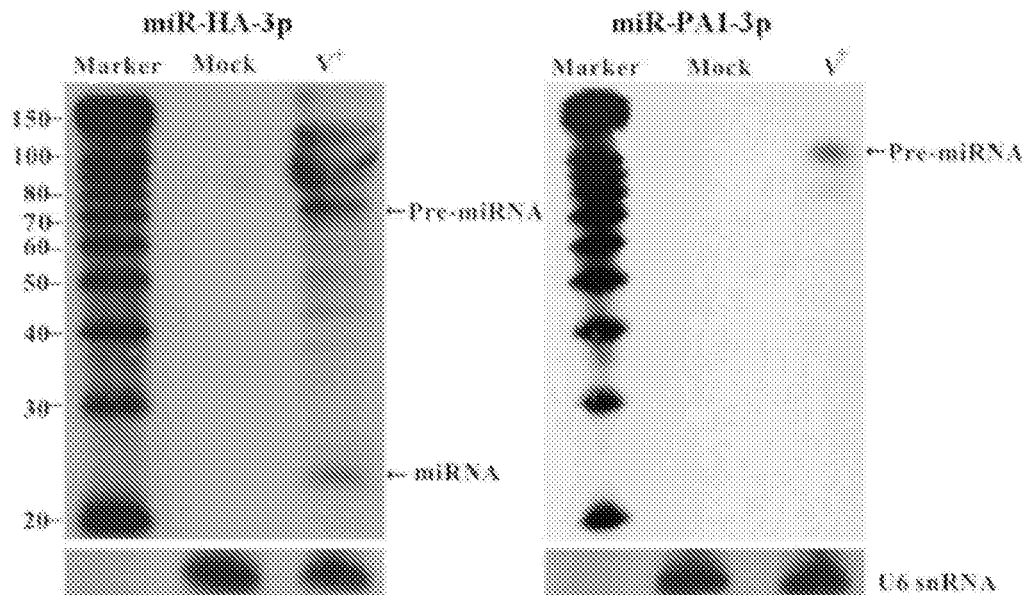
Figure 1:
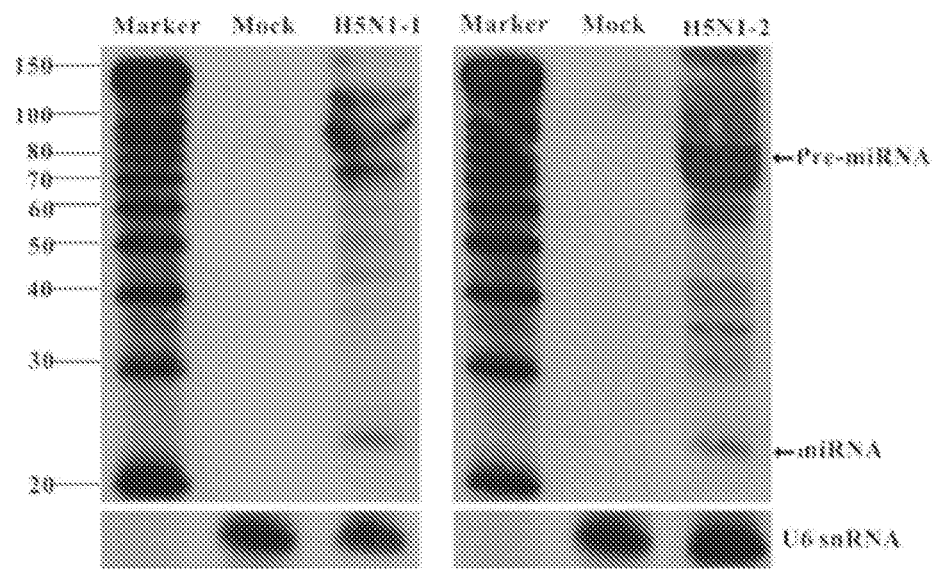

In the figures, "Mut" represents the mutant, "control" represents the control, "Marker" represents the molecular weight standard, and "Mock" represents the blank control.

PARTICULAR EMBODIMENTS

The present inventors are surprised to find during their long and broad research that in vivo pathogens (including infectious microorganisms, parasitic microorganisms, symbiotic microorganisms, etc., such as viruses, bacteria, archaea, chlamydia and protists) will release non-coding RNAs (ncRNAs) including miRNAs, and the specific ncRNAs can serve as biomarkers of in vivo pathogens and can be effectively used for the detection and treatment for the in vivo pathogens, thereby significantly improving the diagnosis and treatment of microbial infectious diseases. The present invention is accomplished on this basis.

In particular, a kind of specific microRNA, miR-HA-3p, is screened for the first time by the present inventor while detecting the microRNA expression levels in samples of animals with avian influenza. Upon examination, it is proved that miR-HA-3p, as a microRNA biomarker, can be very effective in detecting avian influenza virus and avian influenza. Furthermore, inhibiting the function of miR-HA-3p can be very effective in relieving symptoms of avian influenza and treating avian influenza. Based on the microRNA revealed in the present invention for the first time, it can be developed into a detection agent and a therapeutic agent as well as the relating kits for the detection and treatment of avian influenza (e.g., H5N1).

Experiments demonstrate that, after infecting host cells, the H5N1 virus will release a special small molecule miR-HA-3p that will enter the in vivo circulation of host, and the expression level of miR-HA-3p is in direct correlation with the viral infection scale. The present invention further discovers that the target gene of miR-HA-3p is PCBP2, and miR-HA-3p acts on the PCBP2 mRNA to down-regulate the PCBP2 protein expression, resulting in enhanced MAV-mediated anti-virus process, so as to cause an overactive immune response or a cytokine storm during the H5N1 invasion. By constructing a human macrophage model and a mouse model, the present invention confirms that, after blocking miR-HA-3p, the inflammation response of the host can be relieved to increase the survival rate of mice.

By constructing the miR-HA-3p-specific stimulant and inhibitor, the present invention achieves the purpose of regulating the expression level of miR-HA-3p, which can relieve and treat a variety of immune responses and histological lesions induced by the H5N1 virus. This therapy has strong specificity, high efficiency, less side effects and low cost, and this method provides a new idea for human to resist H5N1 virus and its variants.

Terminology

As used herein, the terms "miRNA of the present invention" and "avian influenza H5N1 specific miRNA" can be used interchangeably and refer to miR-HA-3p, including miR-HA-3p-1, miR-HA-3p-2, miR-HA-3p-3, and similar miRNA containing its core sequence (SEQ ID NO.: 4).

As used herein, the terms "inhibitor", "antagonist" and "blocker" can be used interchangeably and bear the same meaning.

As used herein, the terms "miR-HA-3p blocker", "blocker of the present invention" and "inhibitor of the present invention" refer to a substance capable of inhibiting or blocking the function of miR-HA-3p, e.g., an antisense sequence or a nucleic acid sponge. The inhibitors can inhibit the binding of miR-HA-3p with PCBP2 mRNA and the down-regulation of the expression of the target gene PCBP2 by miR-HA-3p.

As used herein, the term "agomir" refers to a miRNA stimulant. Agomir is a specially marked and chemically modified double-stranded small RNA molecule designed referring to the mature microRNA sequences, and is used to simulate the endogenous mature miRNA sequence. Generally, agomir comprises a sequence consistent with the target mature miRNA sequence and a sequence complementary to the mature miRNA sequence. The specific microRNA agomir can be introduced into the cells expressing the corresponding microRNA to simulate the action of microRNA, or be incorporated into a dual luciferase reporter system provided with miRNA binding sites so as to verify the regulation relationship between miRNA and the target gene.

As used herein, the term "antagomir" refers to a miRNA blocker. Antagomir is a specially marked and chemically modified single-stranded small RNA designed referring to the mature microRNA sequence, and is a special efficient blocker for suppressing the endogenous microRNA.

Agomir and antagomir can be designed and synthesized by conventional methods according to the given short RNA sequences.

As used herein, the term "Ago2" refers to argonaute RISC catalytic component 2. It is a main component of the RISC complex, and participates in short-interfering-RNA-mediated gene silencing.

miRNA and its Precursor

The present invention provides a novel miRNA from avian influenza virus. As used herein, said "miRNA" refers to an RNA molecule, which is obtained by processing a transcript that can form a miRNA precursor. The mature miRNA generally has 18-26 nucleotides (nt) (more specifically, about 19-22 nt), not excluding the miRNA molecules having other numbers of nucleotides. MiRNA can generally be detected by Northern blotting.

As used herein, "isolated" means that the substance is isolated from its original environment (if it is a natural substance, the natural environment is the original environment). For example, polynucleotides and polypeptides in the natural environment of living cells are not isolated and purified, but when the same polynucleotides or polypeptides are isolated from other substances coexisting in the natural environment, they are isolated and purified.

MiRNAs can be obtained by processing the precursor miRNAs (pre-miRNAs), and said precursor miRNAs can be folded into a stable stem-loop (hairpin) structure having a general length of 50-100 bp. Said precursor miRNAs can be folded into a stable stem-loop structure, and two sides of stem of the stem-loop structure contain two sequences substantially complementary to each other. Said precursor miRNA may be natural or artificially synthetic.

The precursor miRNA can be cut to generate miRNA, and said miRNA may be substantially complementary to at least a portion of the sequence of the mRNA encoding the gene. As used herein, "substantially complementary" means that the nucleotide sequence is sufficiently complementary and can act upon each other in a predictable manner, e.g., forming a secondary structure (such as a stem-loop structure). Generally, at least 70% of nucleotides in two "substantially complementary" nucleotide sequences are complementary; preferably, at least 80% of nucleotides are complementary; more preferably, at least 90% of nucleotides are complementary; and further preferably, at least 95% of nucleotides are complementary, e.g., 98%, 99% or 100%. Generally, there are at most 40 non-matched nucleotides between two sufficiently complementary molecules; preferably, there are at most 30 non-matched nucleotides; more preferably, there are at most 20 non-matched nucleotides; and further preferably, there are at most 10 non-matched nucleotides, e.g., there are 1, 2, 3, 4, 5 or 8 non-matched nucleotides.

As used herein, the "stem-loop" structure, also known as the "hairpin" structure, refers to a nucleotide molecule which can form a secondary structure comprising a double-stranded region (stem) formed of two regions (on a same molecule) of this nucleotide molecule, the two regions being at two sides of the double-stranded portion; and the structure further comprises at least one "loop" structure, including non-complementary nucleotide molecules, i.e., a single-stranded region. Even if the two regions of the nucleotide molecule are not fully complementary, the double-stranded part of the nucleotide can also maintain the double-stranded form. For example, insertion, deletion, substitution or the like may lead to a non-complementary small region or make the small region itself form a stem-loop structure or another form of secondary structure. However, the two regions can still be substantially complementary to each other and act upon each other in a predictable manner to form a double-stranded region of the stem-loop structure. The stem-loop structure is well known to a person skilled in the art, who can generally determine, being given a nucleic acid having a nucleotide sequence of the primary structure, whether the nucleic acid can form a stem-loop structure.

The miRNA of the present invention has a sequence shown in SEQ ID NOs: 1-3 or the core sequence of SEQ ID NO.: 4. To enhance the stability or other properties of miRNA, at least one protective base, such as "TT", can further be added on at least one end of said miRNA.

Antisense Oligonucleotides

Referring to the miRNA sequence provided in the present invention, the antisense oligonucleotides thereof can be designed. Said antisense oligonucleotides can down-regulate expression of the corresponding miRNA in vivo. As used herein, "antisense oligonucleotides (AS-Ons or ASO)", also known as "antisense nucleotides", refer to DNA molecules or RNA molecules or analogues thereof having a length of about 18-26 nt (more specifically, about 19-22 nt).

In this invention, said "antisense oligonucleotides" further include modified antisense oligonucleotides obtained by locked nucleic acid or nucleic acid chain backbone based modification techniques. Said modification does not substantially alter the activity of antisense oligonucleotides, preferably, said modification can improve the stability, activity or therapeutic effect of antisense oligonucleotides. Locked nucleic acid (LNA) generally refers to a modification technique linking the 2'-oxygen atom with the 4'-carbon atom of ribose through a methylene bridge. LNA can extend the serum half-life of miRNA to improve affinity to the target and reduce the range and extent of off-target effects. Antisense drugs developed with the nucleic acid chain backbone based modification technique are greatly improved in terms of the solubility, resistance to nuclease degradation, etc., and are easy to be synthesized on a large scale. There are many oligonucleotide backbone modification methods, including a thio modification method, e.g., the deoxynucleotide chain is thio modified into a thiodeoxynucleotide chain. In this method, the oxygen atoms of phosphate bonds on the DNA backbone are replaced by sulphur atoms so as to be resistant to nuclease degradation. It should be understood that any modification capable of maintaining most of or all the activity of said antisense oligonucleotides are all included in the present invention.

As a preferred mode of the present invention, the antisense oligonucleotides are subjected to locked nucleic acid modification and more preferably, thio modification.

After being transferred into animal (e.g., a patient with avian influenza) bodies, the antisense oligonucleotides of the present invention can significantly down-regulate the relevant miRNA expression.

Polynucleotide Constructs

Referring to the miRNA sequences provided in the present invention, polynucleotide constructs, which can after transference be processed into miRNAs capable of affecting the expression of the corresponding mRNAs, can be designed, i.e., said polynucleotide constructs can up-regulate the level of the corresponding miRNA in vivo. Therefore, the present invention provides an isolated polynucleotide (construct), said polynucleotide (construct) can be transcribed by human cells into a precursor miRNA which can be cut and expressed as said miRNA in human cells.

As a preferred mode of the present invention, said polynucleotide construct contains a structure shown as formula I:

$$Seq_{forward}\text{-}X\text{-}Seq_{reverse} \qquad \text{Formula I}$$

In formula I, $Seq_{forward}$ is a nucleotide sequence which can be expressed as said miRNA in cells, and $Seq_{reverse}$ is a nucleotide sequence substantially complementary to $Seq_{forward}$; or $Seq_{reverse}$ is a nucleotide sequence which can be expressed as said miRNA in cells, and $Seq_{forward}$ is a nucleotide sequence substantially complementary to $Seq_{reverse}$;

X is a spacer sequence between $Seq_{forward}$ and $Seq_{reverse}$, and said spacer sequence is not complementary to $Seq_{forward}$ and $Seq_{reverse}$;

and after being transferred into cells, the structure shown in the formula I forms a secondary structure as shown in formula II:

Formula II

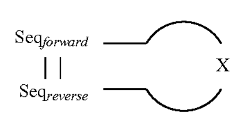

In formula II, $Seq_{forward}$, $Seq_{reverse}$ and X are defined as above;

‖ indicates a complementary base pairing relationship between $Seq_{forward}$ and $Seq_{reverse}$.

Generally, said polynucleotide constructs are located on the expression vector. Therefore, the present invention further comprises a vector containing said miRNA or said polynucleotide constructs. Said expression vector typically further contains a promoter, an origin of replication and/or a marker gene, etc. Methods well known to a person skilled in the art can be used to construct the expression vector required by the present invention. These methods include in vitro recombinant DNA technology, DNA synthesis technology, in vivo recombination technology, etc.

Said expression vector may preferably contain one or more selectable marker genes to provide a phenotypic trait for selection of transformed host cells, such as kanamycin, gentamicin, hygromycin or ampicillin resistance.

Detection Reagent, Detection Chip and Detection Kit

The present invention further provides a kit for the detection of avian influenza virus or avian influenza, said kit containing the detection reagent or detection chip of the present invention. Said kit can be used to detect expression profiles of the miRNA specific to avian influenza of the present invention, or used to detect avian influenza virus or avian influenza. Preferably, said kit further contains a marker to label the RNA sample and a substrate corresponding to said marker.

Furthermore, said kit may further comprise various reagents required for extraction of RNA, PCR, hybridization, colour development, etc., including but not limited to an extraction buffer, an amplification buffer, a hybridization solution, enzymes, a control solution, a developing solution, a washing liquid, antibodies, etc.

Furthermore, said kit further comprises an instruction and/or a chip image analysis software.

Chip

A microRNA expression profile chip generally contains hundreds of, thousands of or more probes, covering a variety of microRNAs, and detects contents of various microRNAs in the sample using the double-stranded homologous complementary principle. Therefore, transcription levels of microRNAs in the sample to be tested can be detected at the same time.

The miRNA sequences of the present invention can also be used to prepare the corresponding miRNA chip and further study the expression profile thereof and the regulation method of miRNAs.

In another aspect, the present invention further provides a chip for analyzing the miRNA expression profile, and said chip can be used to detect avian influenza virus or avian influenza.

The miRNA chip of the present invention comprises a solid-phase carrier and oligonucleotide probes orderly fixed on said solid-phase carrier, said oligonucleotide probes comprising nucleic acid sequences related to the sequences shown in SEQ ID NOs: 1-4.

In particular, a suitable probe can be designed referring to the miRNA of the present invention and is fixed on the solid-phase carrier to form an "oligonucleotide array". Said "oligonucleotide array" refers to an array having addressable locations (i.e., positions characterized by distinguishing accessible addresses), and each addressable location contains one characteristic oligonucleotide associated therewith. The oligonucleotide array can be divided into a plurality of sub-arrays as desired.

Said solid-phase carrier can use various common materials in the gene chip field, such as but not limited to nylon membranes, active group (such as an aldehyde group and an amino group) modified glass or silicon slices, unmodified glass slices, plastic slices, etc.

Said miRNA chip may be prepared by a conventional method for manufacturing biochips known in the field. For example, if the solid-phase carrier uses a modified glass or silicon slice, and the 5' end of the probe contains an amino-modified poly dT string, the oligonucleotide probes can be prepared into a solution, then the solution is applied to the modified glass or silicon slice using a spotter to arrange in a predetermined sequence or array, and then immobilize by standing overnight, so as to obtain the miRNA chip of the present invention.

The solid-phase hybridization between RNA and miRNA chip of the present invention will be carried out according to the conventional method in the art, and a person skilled in the art would readily determine from experience the optimal conditions of buffers, probes, sample concentration, pre-hybridization temperature, hybridization temperature, time, etc. Alternatively, reference can be made to *Molecular Cloning, A Laboratory Manual*.

Then the information to be detected is acquired based on the information about locations of marker signals on the miRNA chip, intensity, etc. If the amplified product is labeled with fluorophores, the information to be detected can also be directly obtained by a fluorescent detection device (such as a laser confocal scanner, Scanarray 3000).

Pharmaceutical Composition

The present invention further provides a pharmaceutical composition comprising a pharmaceutically acceptable carrier or an effective amount of an inhibitor, a blocker or an antagonist for the miRNA (i.e., miR-HA-3p) of the present invention.

As used herein, the term "effective amount" or "effective dose" refers to the amount which can induce a function or activity in human and/or animals and can also be acceptable to human and/or animals.

As used herein, the "pharmaceutically acceptable" component is applicable to human and/or animals (e.g., mammals and poultry) without excessive adverse side effects (such as toxicity, irritation and allergic response), i.e., a substance with a reasonable benefit/risk ratio. The term "pharmaceutically acceptable carrier" refers to a carrier for the administration of a therapeutic agent, including various excipients and diluents.

The pharmaceutical composition of the present invention contains safe and effective amount of the active component of the present invention and a pharmaceutically acceptable carrier. Such carrier includes, but is not limited to, saline, buffer, glucose, water, glycerol, ethanol, and a combination thereof. Generally, a pharmaceutical preparation shall match with the mode of administration, and the dosage form of the pharmaceutical composition of the present invention can be injection, oral preparation (tablet, capsule, or oral liquid), transdermal agent, or slow release agent. For example, preparation is performed by a conventional method using physiological saline or an aqueous solution containing glucose and other adjuvants. Said pharmaceutical composition is preferably produced under sterile conditions.

The effective amount of the active component of the present invention may vary depending on the mode of administration and the severity of the disease to be treated. A person skilled in the art could determine the selection of the preferred effective amount depending on various factors (e.g., by clinical trials). Said factors include, but are not limited to, the pharmacokinetic parameters of said active compound, e.g., bioavailability, metabolism, half-life, etc.; and the severity of the patient's disease to be treated, the patient's weight, the patient's immune state, the administration route, etc. Generally, when the active component of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered daily, or the dosage is reduced proportionally.

The pharmaceutically acceptable carriers of the present invention include, but are not limited to, water, saline, liposomes, lipids, proteins, protein-antibody conjugates, peptides, cellulose, nanogels, or a combination thereof. The choice of carriers should match the mode of administration, which would be well known to a person skilled in the art.

The present invention further provides the use of said pharmaceutical composition for the preparation of a medicament for treating avian influenza, alleviating the symptoms of avian influenza, reducing the number of avian influenza viruses in host animals and reducing the mortality of avian influenza, and for reducing overactive immune responses.

The main advantages of the present invention include:

(a) the present invention provides a kind of specific microRNA for avian influenza virus H5N1, i.e. miR-HA-3p.

(b) the miRNA of the present invention can be used as a marker for the detection of avian influenza virus or avian influenza, and is very effective in detecting avian influenza virus or avian influenza.

(c) the miRNA of the present invention can also be used as a target for the treatment of avian influenza, and an inhibitor (or blocker) for the miRNA of the present invention can be used for the targeted therapy of H5N1 induced diseases.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., *Molecular Cloning: A Laboratory Manual* (New York: Cold Spring Harbour Laboratory Press, 1989), or the conditions recommended by the manufacturer are followed. All percentages and portions are of weight unless otherwise indicated.

Example 1. Screening and Detection for miRNAs Encoded by H5N1

Firstly, miRs encoded by H5N1 are screened by computer modeling. The expression levels of screened miRs in multiple H5N1-infected cells are detected by real-time quantitative PCR; and the expression level of miR-HA-3p is verified by RNA blotting.

1.1 Experimental Method:

1). Using a computer modeling software, and referring to the four subtypes (H1N1, H3N2, H5N1 and H9N2) of H5N1 influenza virus, unknown miRNA precursors are compared with known miRNA precursors in terms of structure and similarity, 18 specific miRNA precursor candidates encoded by H5N1 are obtained, and corresponding miRNAs are predicted. Real-time quantitative PCR is performed for the 18 candidate miRNAs to detect whether H5N1 infected cells contain the predicted miRNAs, and the RNA samples used are extracted from H5N1 infected HEK293A, HEK293T, A549 and MDCK cells. The miRNA expression detection uses U6 as a reference gene.

2). For miR-HA-3p, the miRNA obtained through screening with a significant change in the expression level, its expression levels in serum of patients at severe H5N1 infection stage and in convalescent stage are measured by real-time quantitative PCR.

3). The expression of target miRNAs in the H5N1-infected cells is detected by RNA blotting again.

4). To confirm with RNA blotting that miR-HA-3p not only exists in specific H5N1 influenza viruses, the present inventor extracts small RNA fragments (<200 nt) from H5N1-infected A549 cells, and hybridize these fragments with the corresponding miR-HA-3p probes.

1.2 Experimental Results:

The detailed results are shown in FIG. 1.

1). FIG. 1A shows the predicted secondary structure of the stem-loop structure of the H5N1 miRNA precursor. The prediction is carried out with software Mfold, and the 5' and 3' ends of the predicted mature miRNA are marked with red and blue colors, respectively. The result of FIG. 1A indicates that, in the three predicted precursors, one is encoded by the HA fragment, and the other two are encoded by the PA fragment. Each candidate miRNA can be folded into a stable specific hairpin structure.

FIG. 1B shows expression levels of the 18 miRNA candidates after the invasion of H5N1 virus into four kinds of cells, and it can be seen from FIG. 1B that miR-HA-3p and miR-PA1-3p can be stably detected in cells in 24 hours after infection, while the other 16 kinds of miRNA have a low expression.

miR-HA-3p has three particular sequences as follows:

```
miR-HA-3p-1:
                                         (SEQ ID NO.: 1)
AGGACUAUUUGGAGCUAUAGCA miR-HA-3p-2:
                                         (SEQ ID NO.: 2)
GGACUAUUUGGAGCUAUAGCAG miR-HA-3p-3:
                                         (SEQ ID NO.: 3)
GAGGACUAUUUGGAGCUAUAGC
```

The core sequence of the above-mentioned three miRNAs is GGACUAUUUGGAGCUAUAGC (SEQ ID NO.: 4).

FIG. 1C shows the results of the expression levels of miR-HA-3p and miR-PA1-3p measured at different time points after viral infection, and FIG. 1C indicates that the expressions of miR-HA-3p and miR-PA1-3p are gradually increasing in the H5N1-infected A549 cells at different points of time during the infection, and the expression of miR-HA-3p is higher than the expression of miR-PA1-3p at each point of time after infection.

2). FIG. 1D shows the absolute value of miR-HA-3p in the serum of a patient in the convalescent state, and FIG. 1D indicates that the expression of miR-HA-3p in the serum of the patient at the severe infection (acute) stage is very high, but when the viral infection is decreased, miR-HA-3p is barely detectable.

3). FIG. 1E shows the expression levels of miR-HA-3p and miR-PA1-3p in 24 hours after the co-infection of A549 cells analyzed by RNA blotting; the column at the most left of the figure is of the markers. FIG. 1E indicates that miR-HA-3p precursor miRNA of about 80 nt and 22-nt mature miR-HA-3p can be quickly detected from the H5N1-infected A549 cells. The precursor miR-PA1-3p RNA of about 100 nt can also be detected; however, the mature miR-PA1-3p cannot be detected. The RNA blotting result is consistent with the real-time quantitative PCR result.

4). FIG. 1F shows the expression levels of miR-HA-3p measured with RNA blotting after A549 cells are infected with two strains respectively. The result of FIG. 1F shows that miR-HA-3p can be produced after the host is infected with both H5N1 IAV isolated strains.

The multiple experiments above demonstrate that, after infecting host cells, the avian influenza H5N1 will release a special small molecule miR-HA-3p that will enter the in vivo circulation of hosts, and that the expression level of miR-HA-3p is in positive correlation with the viral infection degree.

Example 2. Prediction and Verification of miR-HA-3p Target Sites

In this example, the miR-HA-3p target sites are predicted and verified. Mouse and human PCBP2 mutant strains are constructed, the relationship between PCBP2 and the quantity of miR-HA-3p is detected by detecting luciferase activity; and the relationship between the expression amount of the protein corresponding to the target gene and the quantity of miR-HA-3p is detected by Western blotting.

2.1 Experimental Method:

1). miR-HA-3p target sites are predicted by computer modeling.

2). To examine whether miR-HA-3p can regulate the expression of PCBP2, mouse and human PCBP2 mutant strains are respectively constructed, then PCBP2 wild type and mutant strains are treated with agomiR-HA-3p (a miR-HA-3p stimulant) and agomiR-HA-3p (M) (a mutated miR-HA-3p stimulant) respectively. The relationship between PCBP2 and the quantity of miR-HA-3p is detected by detecting the luciferase activity. The relationship between the expression amount of the protein corresponding to the target gene and the quantity of miR-HA-3p is detected by Western blotting.

3). To determine that the down-regulation of the PCBP2 protein expression is caused by miR-HA-3p, the content of PCBP2 protein in A549 cells containing miR-HA-3p is detected by Western blotting. As a control, an RNAi system for silencing PCBP2 gene is constructed.

4). To obtain the direct evidence of miR-HA-3p using PCBP2 as the target site, the present inventor further carries out RNA binding protein immunoprecipitation tests to detect a complex of PCBP2 mRNA and Ago2 that is an RNA-induced silencing complex, with miR-16 as a control.

Figure 2:
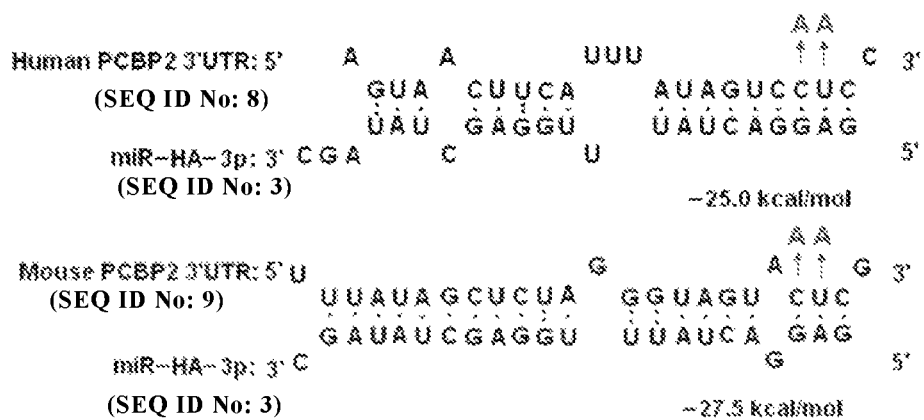
FIG. 2 shows the inhibiting effect of miR-HA-3p on a target gene PCBP2.
Figure 2:
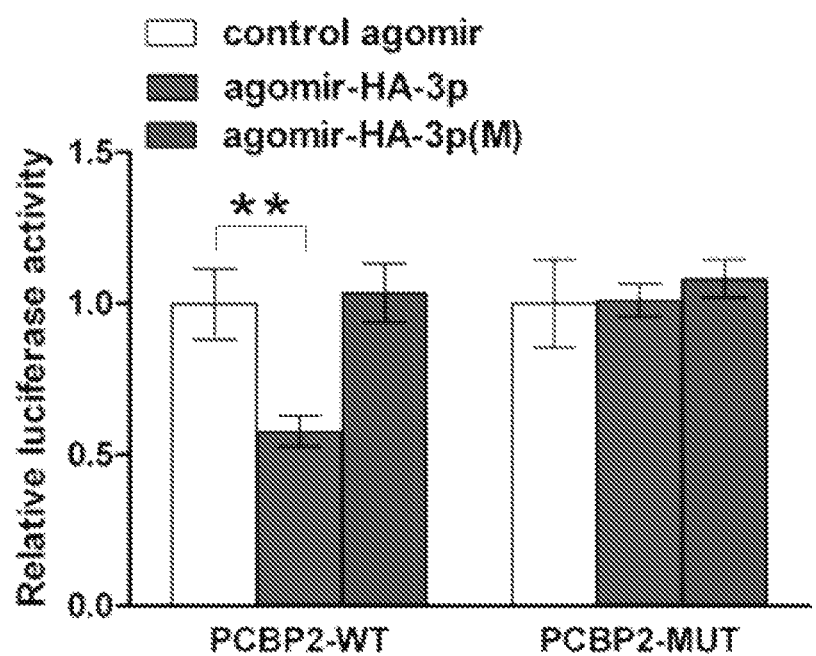
Figure 2:
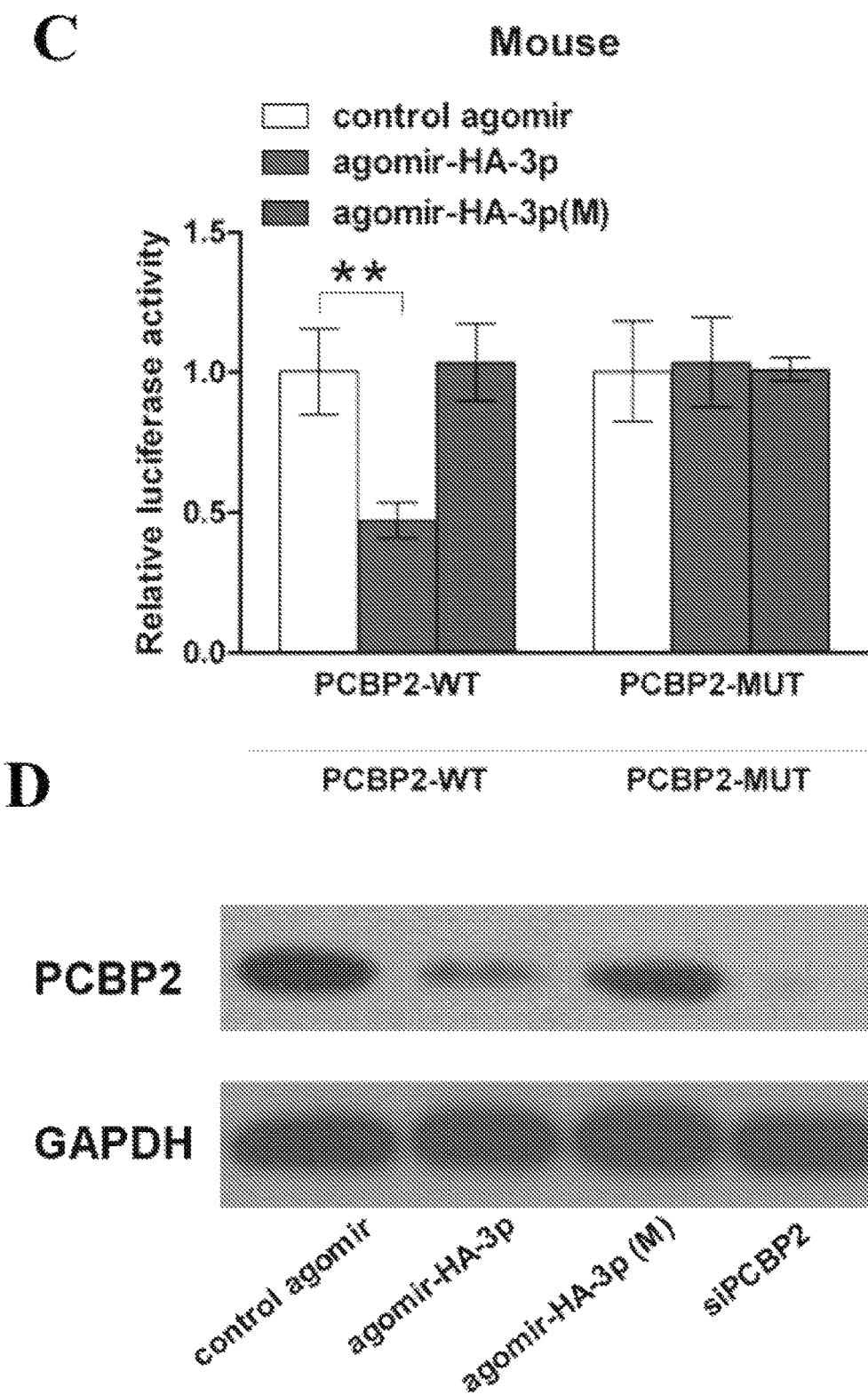
Figure 2:
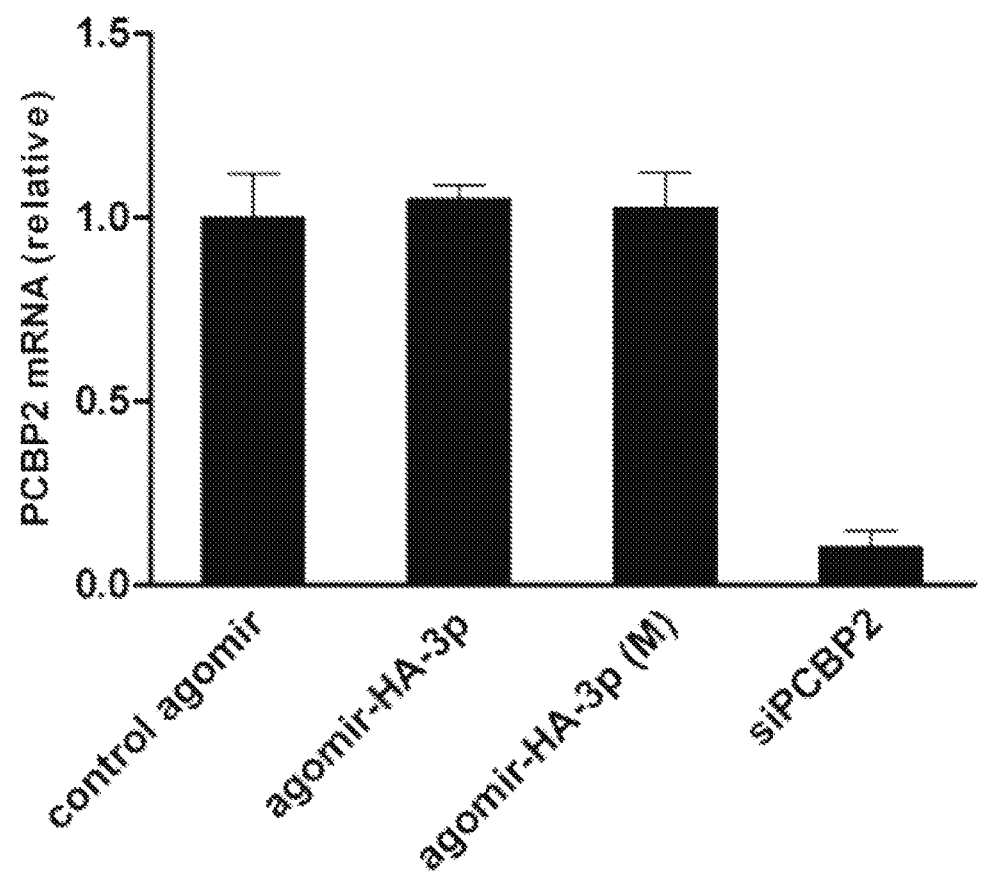
Figure 2:
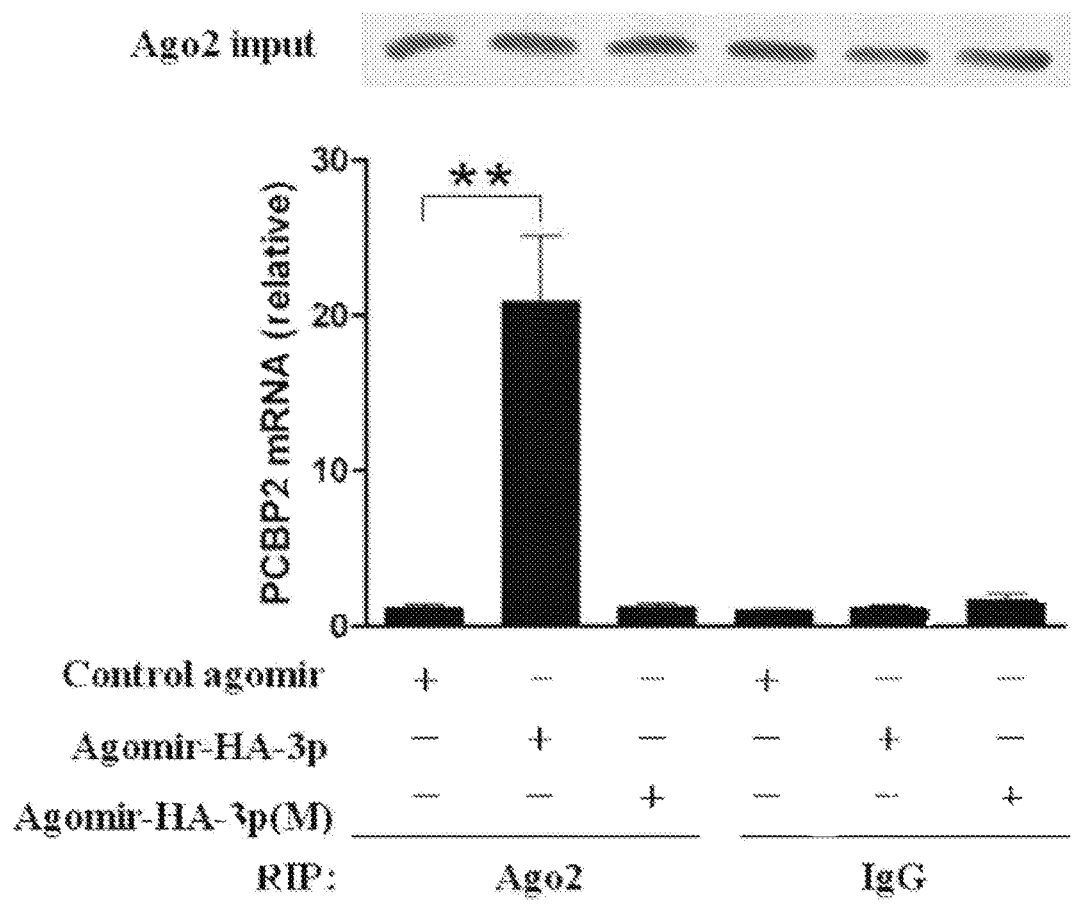

2.2 Experimental Results:

The detailed results are shown in FIG. 2.

1). FIG. 2A shows binding sites of miR-HA-3p and the 3' ends of human and mouse PCBP2 mRNA, and FIG. 2A indicates that it is found after prediction that PCBP2 mRNA is a potential target site of miR-HA-3p.

2). FIG. 2B shows the luciferase activities of the HEK293T cells transfected with wild type and mutant type human PCBP2 genes after being treated with agomiR, agomiR-HA-3p and agomiR-HA-3p (M), respectively. FIG. 2B indicates that the agomiR-HA-3p in human models can significantly down-regulate the expression of wild-type PCBP2. However, agomiR-HA-3p (M) causes no such effect.

FIG. 2C shows the luciferase activities of the HEK293T cells infected with wild type and mutant type mouse PCBP2 genes after being treated with agomiR, agomiR-HA-3p and agomiR-HA-3p (M), respectively. FIG. 2C indicates that the agomiR-HA-3p in mouse models can significantly down-regulate the expression of wild-type PCBP2. However, agomiR-HA-3p (M) causes no such effect.

3). FIG. 2D shows the result of the PCBP2 protein levels in A549 cells treated with agomiR, agomiR-HA-3p and agomiR-HA-3p (M), analyzed by Western blotting. The result of FIG. 2D indicates that the expression of PCBP2 is significantly suppressed after the A549 cells are transfected with agomiR-HA-3p, and the expression of PCBP2 in cells transfected with agomiR-HA-3p (M) has no significant change.

FIG. 2E shows the expression levels of PCBP2 mRNA in A549 cells after being treated with agomiR, agomiR-HA-3p and agomiR-HA-3p (M).

4). FIG. 2F shows the result of real-time quantitative PCR for PCBP2 mRNA obtained by immunoprecipitation reaction in A549 cells treated with agomiR, agomiR-HA-3p and agomiR-HA-3p (M); and the control result is the result of the agomiR-treated A549 cells obtained by immunoprecipitation with IgG. The result of FIG. 2F indicates that, for the A549 cells transfected with agomiR-HA-3p, when the miR-HA-3p is over-expressed, the PCBP2 mRNA and Ago2 complex is enriched by approximately 20-fold, suggesting that the miR-HA-3p and PCBP2 mRNA are reacted in the RNA-induced silencing complex and regulate the post-transcriptional level of PCBP2 protein. In line with expectations, the experimental group with agomiR-HA-3p removed shows no enrichment of the PCBP2 mRNA and Ago2 complex.

The result above indicates that miR-HA-3p can act directly on the 3' end of PCBP2 mRNA, suggesting that miR-HA-3p plays a role in the inhibition of translation. PCBP2 belongs to the nucleoprotein E family, and is related with the MAV-mediated antiviral effect. H5N1 can enhance the MAV mediated anti-virus process by silencing PCBP2, so as to cause an excessive immune response or cytokine storm in the H5N1 invasion process.

Example 3. Demonstration of miR-HA-3p Regulating the Secretion of Cytokines During the H5N1 Infection Using a Macrophage Model In this example, to verify the effect of miR-HA-3p on cytokines, the following experiment is carried out using human macrophages as an in vitro model.

3.1 Experimental Method:

1). Differentiated macrophages are treated with agomiR, agomiR-HA-3p and agomiR-HA-3p (M) respectively, and the intracellular miR-HA-3p levels are detected by real-time quantitative PCR in 24 hours after transfection.

2). To detect the effect of miR-HA-3p on the expression of target protein during the virus infection, the present inventor constructs a H5N1 virus mutant using reverse genetics. To detect the in vitro replication effect of the mutant, the present inventor carries out co-infection for the macrophages with the wild-type and mutant virus strains. Virus titer (titer) is detected by virus titration experiments after 48 hours.

3). The intracellular expression level of miR-HA-3p is detected after the macrophages are infected with wild-type H5N1 and mutant H5N1 strains.

4). Before viral infection, the present inventor treats the macrophages with antagomiR-HA-3p (a miR-HA-3p blocker) and antagomiR (a miR blocker) respectively. Then the expression level of PCBP2 in several treatment groups is detected in 24 hours and 48 hours after the viral infection.

5). The transcriptional levels of TNF-α, IL-6 and other cytokines, such as IFN-β and IL-1β in each treatment group are detected at several specific points of time after infection.

6). The contents of TNF-α, IFN-β and IL-6 in the macrophage culture supernatants of each treatment group are detected at several specific points of time after infection.

Figure 3:
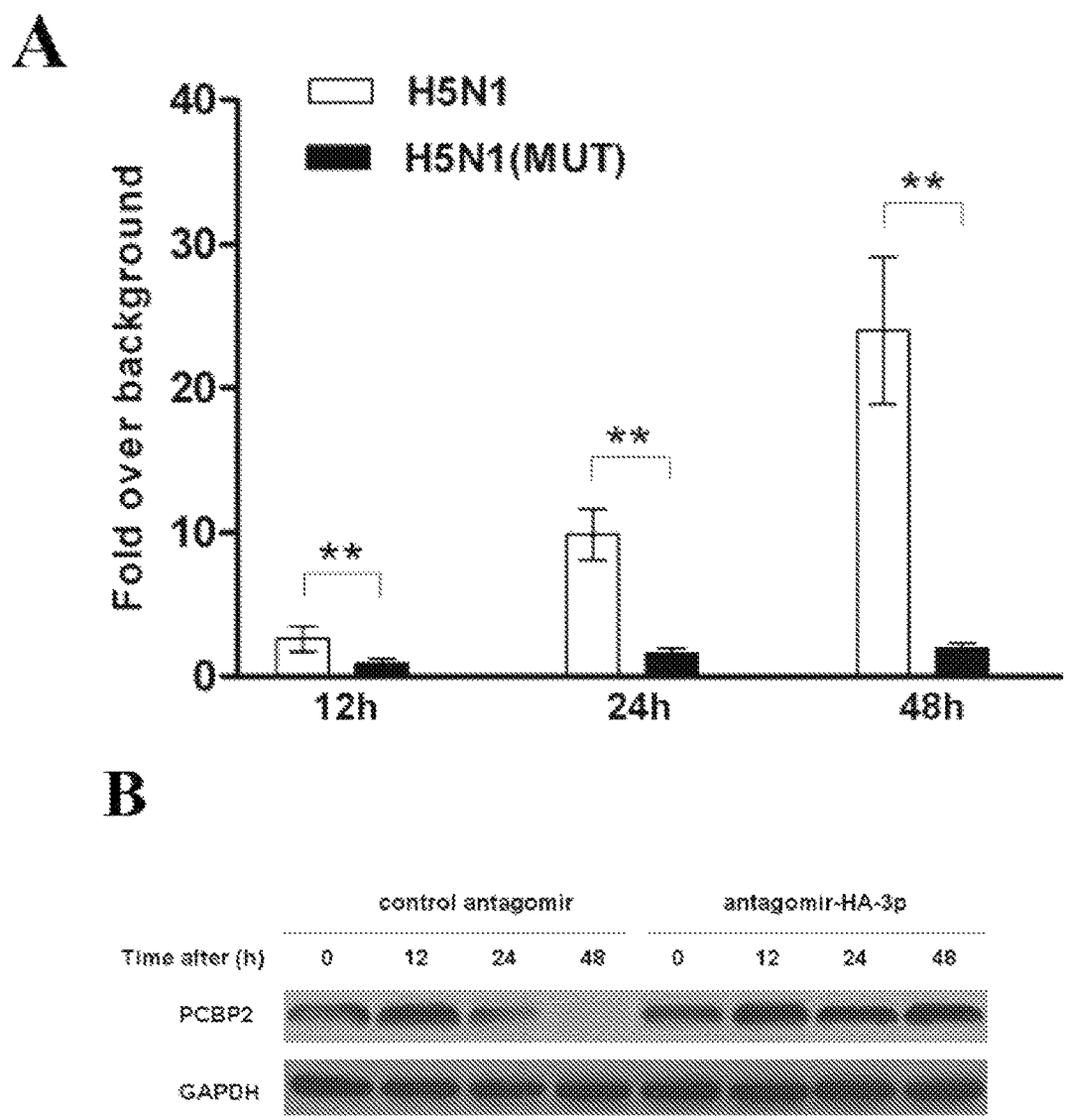
FIG. 3 shows the effect of miR-HA-3p on cytokine secretion in macrophages infected with H5N1 wild type and a mutant strain.
Figure 3:
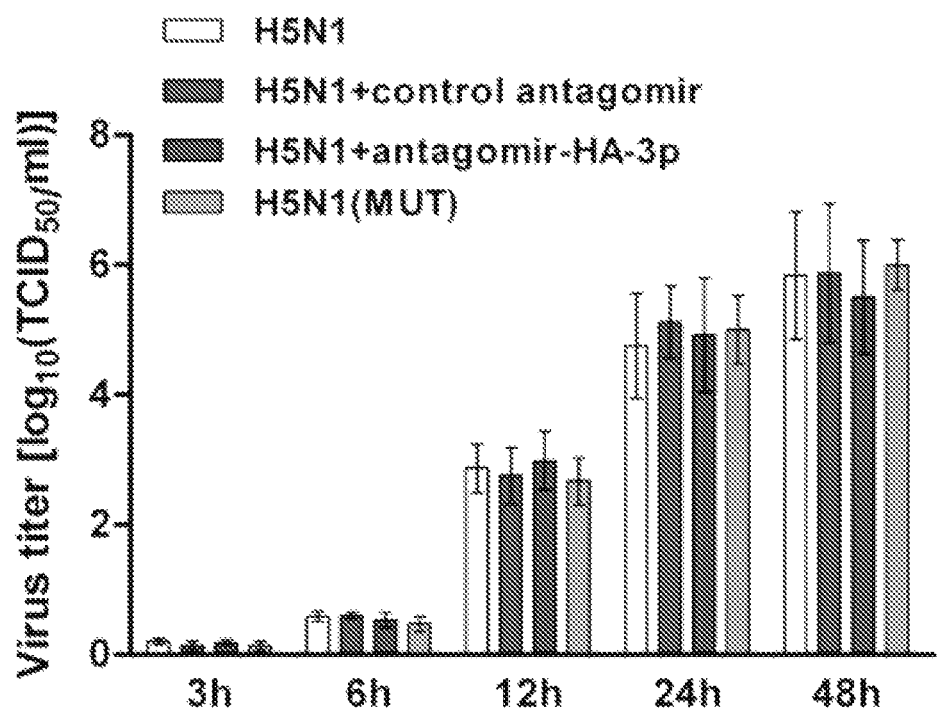
Figure 3:
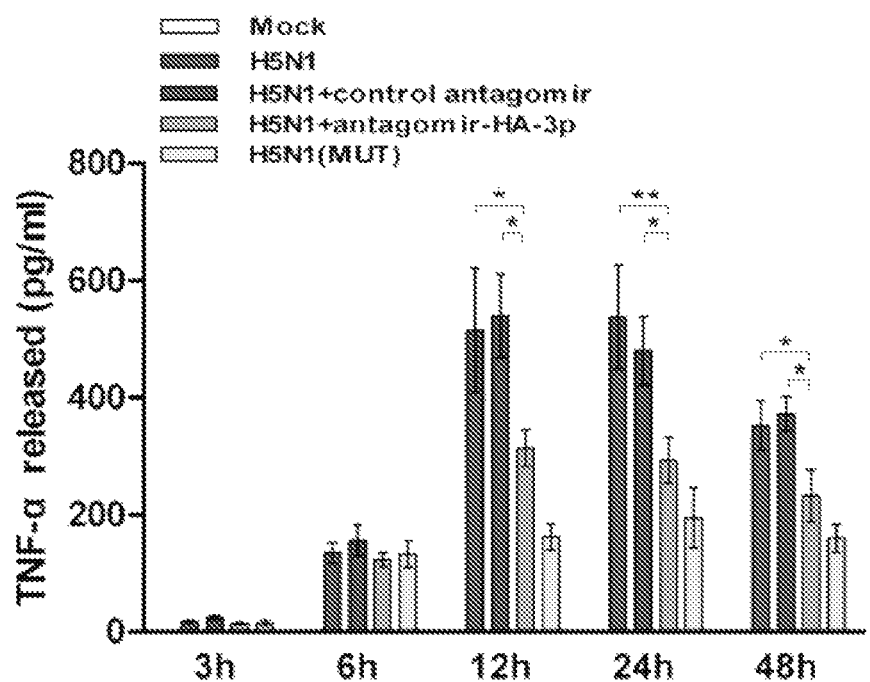
Figure 3:
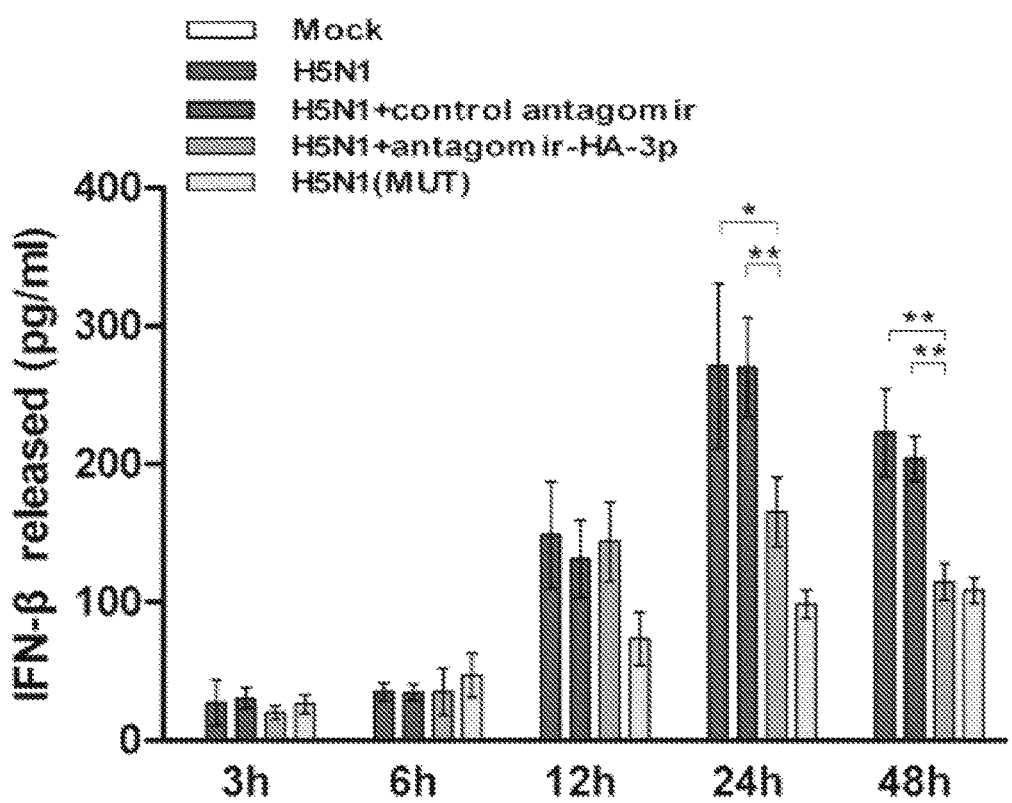
Figure 3:
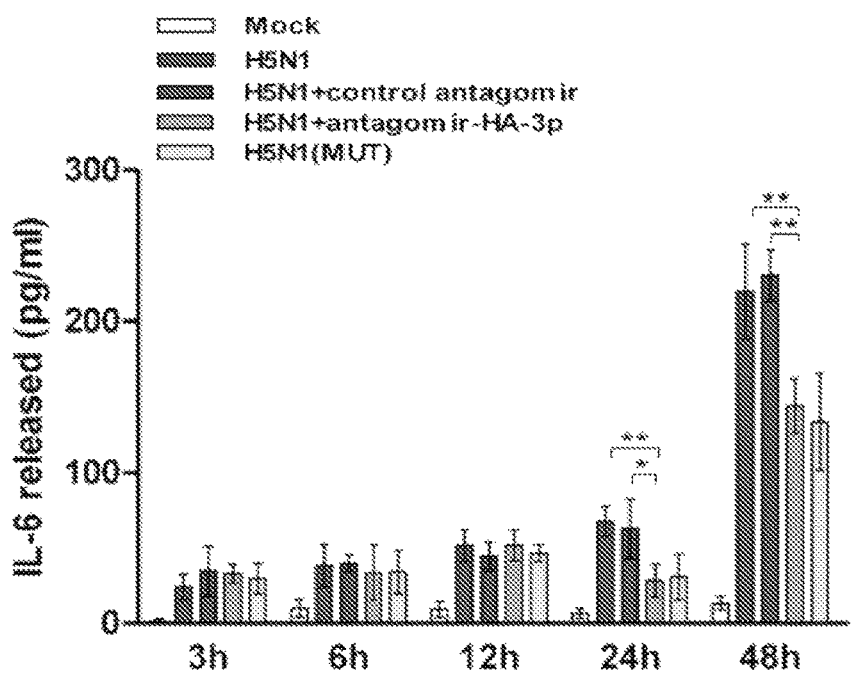
Figure 4:
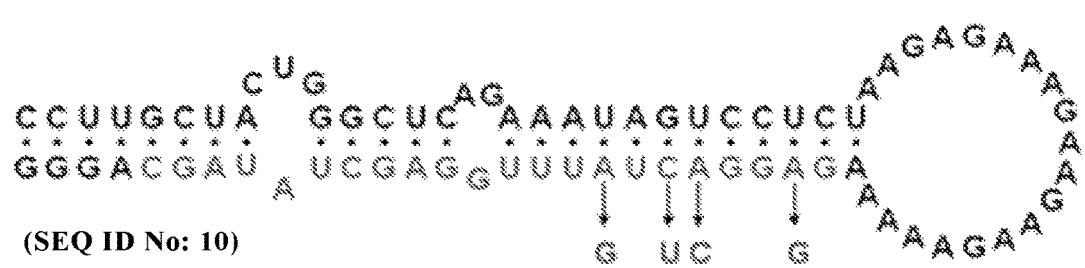
FIG. 4 shows the expression of PCBP2 after treatment with a miR-HA-3p inhibitor.
Figure 4:
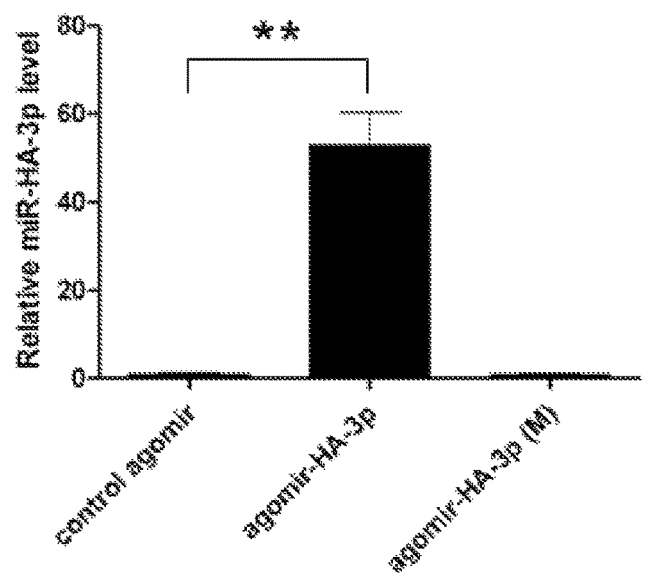
Figure 4:
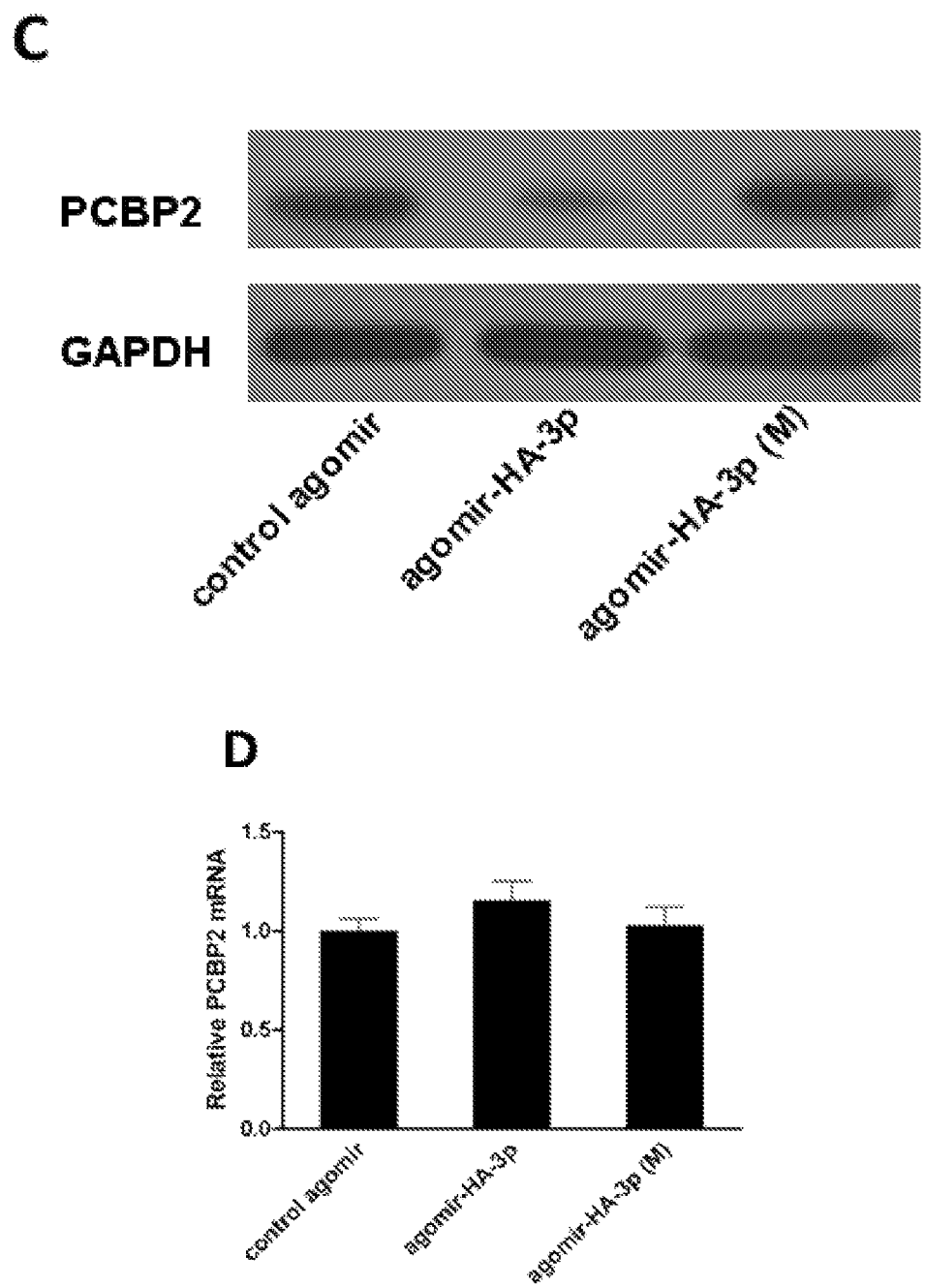
Figure 5:
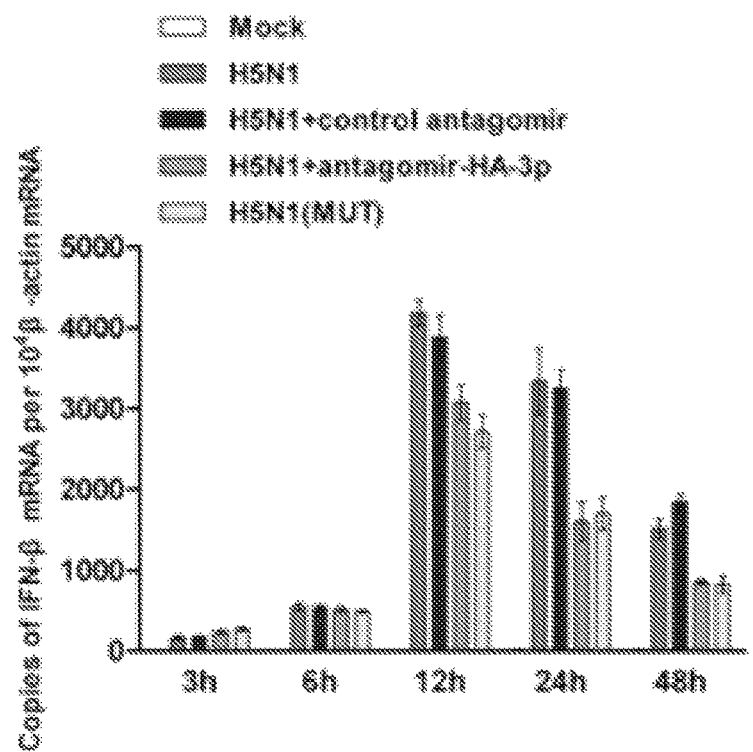
FIG. 5 shows the expression levels of TNF-α, IFN-β, IL-1β or IL-6 mRNA in the macrophages infected with H5N1 or an H5N1 mutant strain under different treatment conditions.
Figure 5:
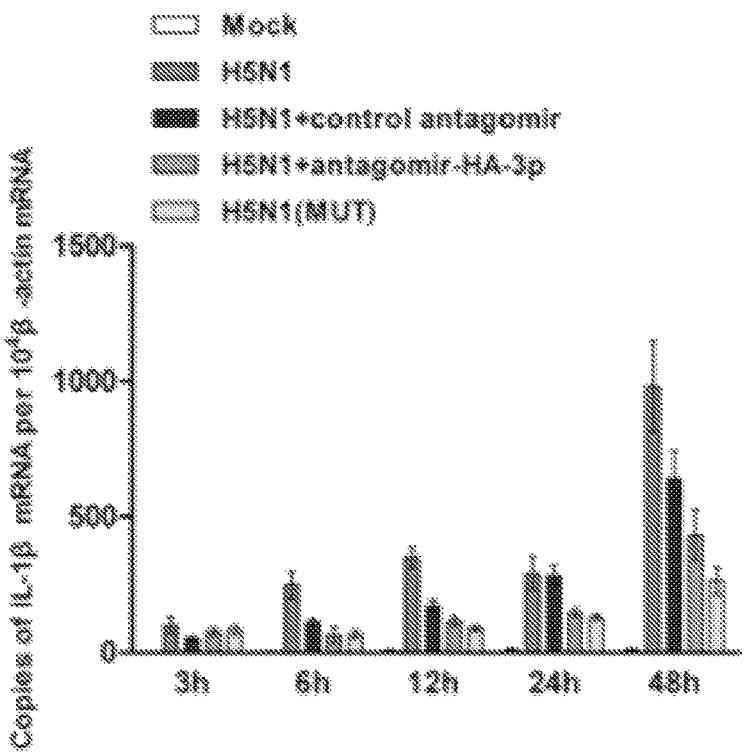
Figure 5:
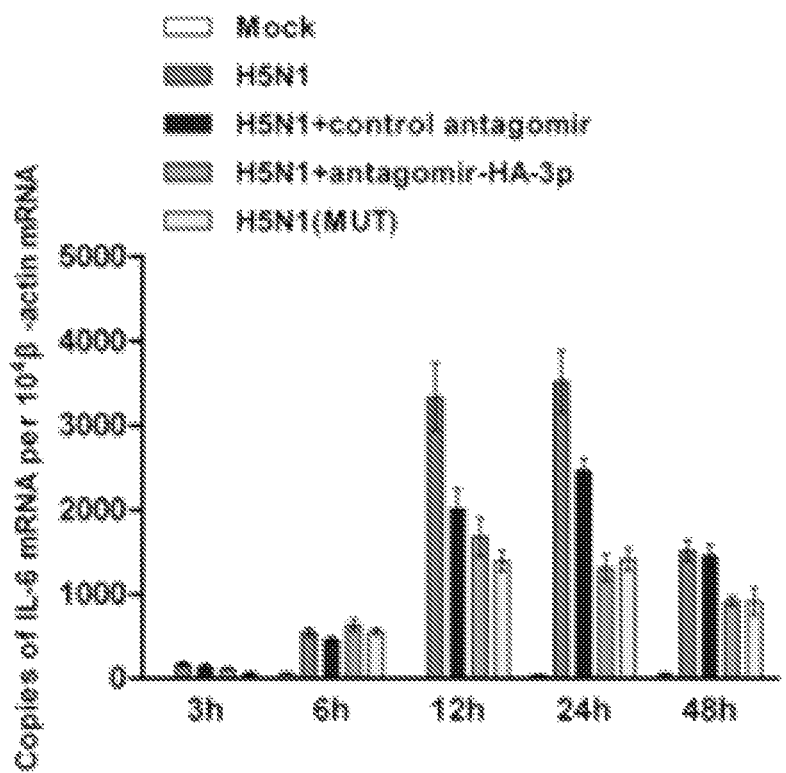

3.2 Experimental Results:

The detailed results are shown in FIGS. 3, 4 and 5.

1). FIG. 4A shows a schematic diagram of principle of the agomiR-HA-3p mutation sequence and the mutation points of H5N1 mutant strain.

FIG. 4B shows the expression levels of miR-HA-3p in macrophages of the agomiR, agomiR-HA-3p or agomiR-HA-3p (M) treatment group in 24 hours after electroporation. The result of FIG. 4B indicates that the content of miR-HA-3p in the agomiR-HA-3p treatment group is significantly increased in 24 hours after transfection, and the intracellular level of miR-HA-3p in the agomiR or agomiR-HA-3p (M) treatment group remains stable.

FIG. 4C shows the PCBP2 protein level in macrophages in the agomiR, agomiR-HA-3p or agomiR-HA-3p (M) treatment group in 48 hours after electroporation. It can be seen from FIG. 4C that the PCBP2 protein expression in the agomiR-HA-3p treatment group is significantly lower than that in the agomiR or agomiR-HA-3p (M) treatment group.

FIG. 4D shows the PCBP2 mRNA expression level in macrophages in the agomiR, agomiR-HA-3p or agomiR-HA-3p (M) treatment group in 48 hours after electroporation. The result of FIG. 4D indicates that the PCBP2 mRNA levels in the three treatment groups show no significant change.

2). FIG. 4E shows the titers of macrophages infected with H5N1 (wild-type) or an H5N1 mutant in 48 hours after infection. The result suggests that the wild-type H5N1 strain causes no significant difference from the mutant H5N1 strain.

3). FIG. 3A shows the expression levels of miR-HA-3p in macrophages infected with H5N1 and mutant strain at different points of time after infection. The result of FIG. 3A indicates that the expression level of miR-HA-3p in macrophages infected with wild-type H5N1 virus in 24 hours after the infection, and the expression level of miR-HA-3p in macrophages infected with the mutant strain remains substantially unchanged.

4). FIG. 3B shows the analysis result of PCBP2 protein level in macrophages treated firstly with antagomiR or antagomiR-HA-3p and then H5N1 at different points of time after infection. It can be seen from FIG. 3B that the PCBP2 protein level in the antagomiR-HA-3p treatment group is significantly higher than that in the antagomiR treatment group in 24 hours and 48 hours after virus infection.

FIG. 3C shows the virus titers in cells infected with H5N1 measured by TCID50 method at different points of time after infection.

5). FIGS. 3D-F show the levels of TNF-α, IFN-β and IL 6 in the cell supernatants in different treatment groups treated with H5N1 or an H5N1 mutant. It can be seen from FIGS. 3D-F that the cytokine concentrations in the antagomiR-HA-3p treatment group are lower than those in the antagomiR treatment group. In fact, the contents of TNF-α, IFN-β and IL-6 in the macrophage culture supernatants in the antagomiR-HA-3p treatment group are equivalent to the contents of corresponding cytokines in the groups infected with the mutant strain.

6). FIG. 5 shows the expression levels of TNF-α, IFN-β, IL-1β or IL-6 mRNA in the macrophages infected with H5N1 or an H5N1 mutant under different treatment conditions. The result of FIG. 5 shows that the transcriptional level of TNF-α in the antagomiR-HA-3p treatment group is down-regulated, and in 24 hours after infection the content of IL-6 mRNA in macrophages in the antagomiR-HA-3p treatment group is about 60% of the content in the antagomir treatment group. A similar phenomenon is also observed by other cytokines such as IFN-β and IL-1β.

The experimental results above suggest that, compared with patients with common influenza, the levels of cytokines and inflammatory chemokine factors in the serum of patients infected with H5N1 virus are significantly higher. This experiment confirms that the miR-HA-3p produced by the H5N1 virus during infection plays a regulatory role on the RIG-I signaling system to promote the production of cytokines. Since PCBP2 plays an important regulatory role in RIG-I signaling system, miR-HA-3p functions by acting on PCBP2.

Example 4. Demonstration of the Direct Correlation Between miR-HA-3p and the H5N1 Infection Degree Using Mouse Models In this example, the function of miR-HA-3p in the abnormal cytokine regulation induced by the in vivo H5N1 infection is detected using the established mouse model. Real-time quantitative PCR, histological detection, ELISA and virus titer titration are mainly used as follows.

4.1 Experimental Method:

1). Female BAL b/c mice are intranasally inoculated with lethal doses of H5N1 (wild-type) and the H5N1 mutant, and then their body weight, mortality, viral replication and cytokine polymer are detected. In 8 hours after virus invasion, each of the two groups of mice inoculated with H5N1 and the H5N1 mutant are divided into two sub-groups, which are injected with a miR-HA-3p blocker and a miR blocker respectively for five consecutive days.

2). The virus titer in the lung homogenates of mice in each treatment group is further measured. There are seven experimental groups in total, including six treatment groups: H5N1, H5N1 (MUT), H5N1+control antagomir, H5N1 (MUT)+control antagomiR, H5N1+antagomiR-HA-3p, and H5N1 (MUT)+antagomiR-HA-3p, and one PBS treatment group as the control group.

3). Histological examination for the mice in the seven experimental groups is performed.

4). To determine whether the cytokines produced during viral infection are related with the miR-HA-3p, the concentrations of four cytokines, TNF-α, IL-1β and IL-6, are measured for the seven experimental groups at multiple points of time after infection.

Figure 6:
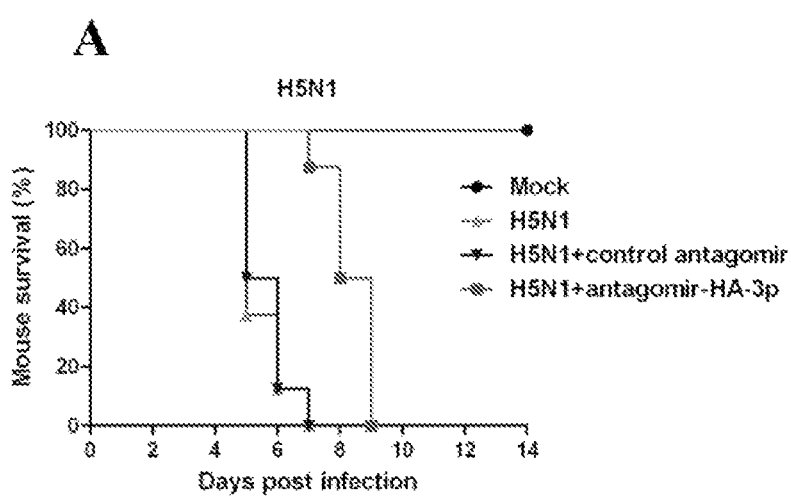
FIG. 6 shows that the miR-HA-3p is in direct correlation with the H5N1 infection degree in a mouse model.
Figure 6:
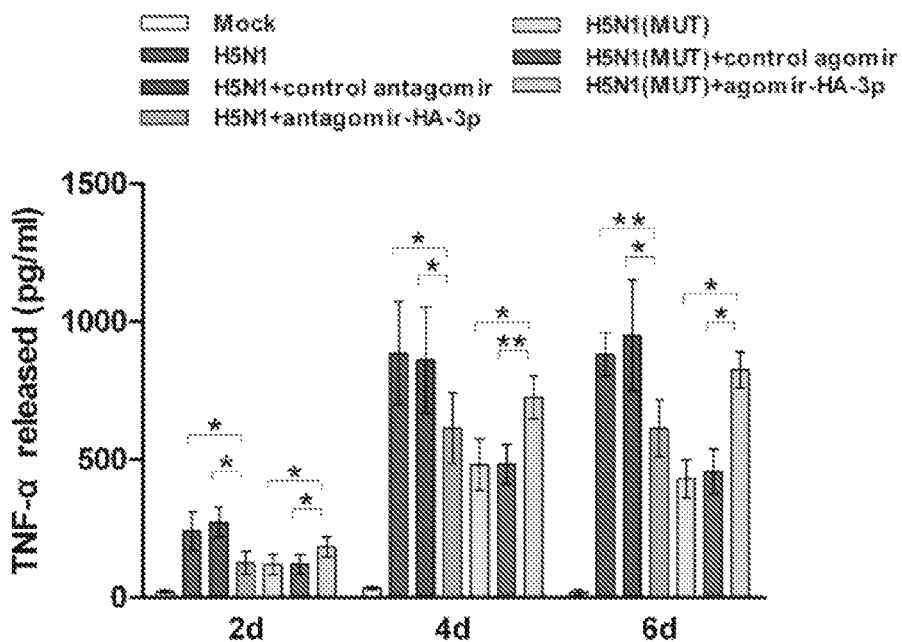
Figure 6:
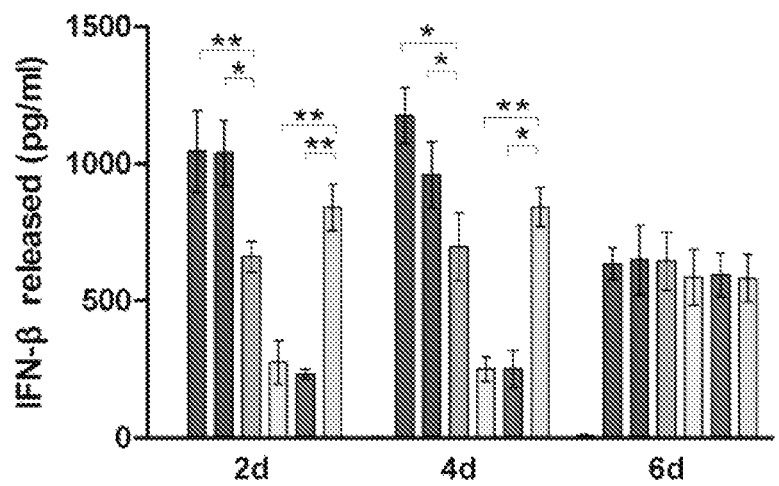
Figure 6:
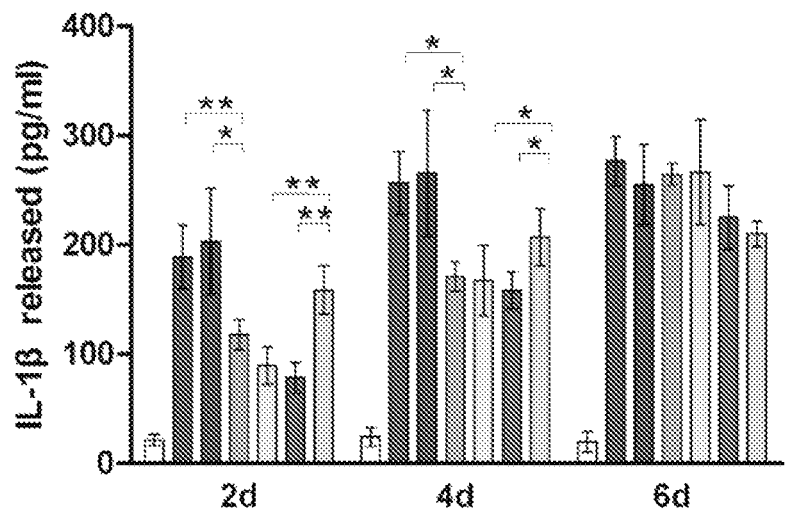
Figure 6:
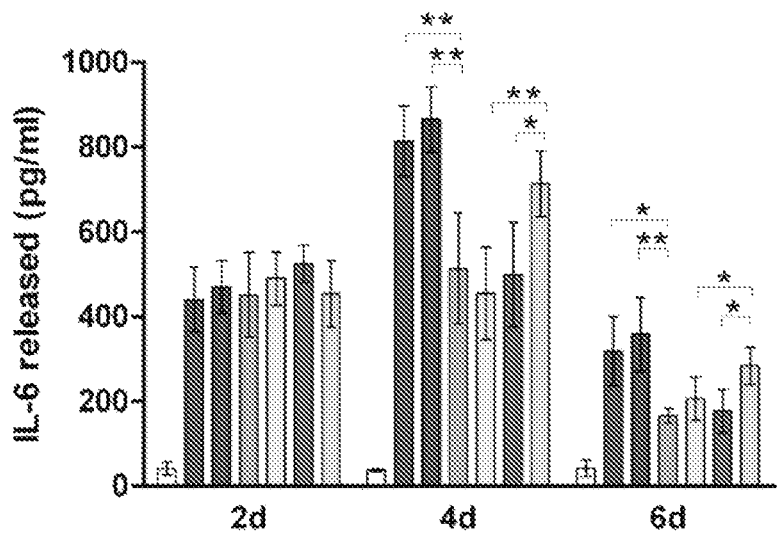

4.2 Experimental Results:

The detailed result of the above-mentioned experimental method 1 is shown in FIG. 6:

FIGS. 6 (A, B) shows the mortality of mice inoculated with H5N1 or the mutant strain under different treatment conditions. FIGS. 6 (C, D) shows the degree of weight loss of mice inoculated with H5N1 or the mutant strain under different treatment conditions.

FIGS. 6 (E-H) shows the levels of four cytokines (TNF-α (E), IFN-β (F), IL-1β (G) and IL-6 (H)) measured by ELISA assay in lungs of the mice inoculated with H5N1 or the mutant strain under different treatment conditions.

The detailed results are analyzed as follows:

1). FIG. 6A shows that, in seven days after inoculation, the death rate of mice in the H5N1 treatment group is 100%, and FIG. 6C shows that the mice in the H5N1 treatment group have no less than 20% of weight loss. The death rate and weight loss of the mice in the (H5N1+control antagomiR) treatment group are equivalent to those of the mice in the H5N1 treatment group, while the mice in the (H5N1+antagomiR-HA-3p) treatment group have certain weight loss after 7 days, but their death rates are only about 10%. FIGS. 6A and 6C show that, compared with the mice in the H5N1 treatment group, the mice in the H5N1 (MUT) treatment group has longer survival time and slower weight loss rate. FIG. 6B shows that, after being further injected with the miR-HA-3p stimulant, the survival rate of the mice in the H5N1 (MUT) treatment group is significantly decreased; FIG. 6D shows that, after being further injected with the miR-HA-3p stimulant, the weight loss rate of the mice in the H5N1 (MUT) treatment group is faster; and the same as expected, FIG. 6B shows that, after being further injecting with the miR stimulant, the survival rate and body weight of the mice in the H5N1 (MUT) treatment group have no significant change.

2). FIGS. 6E-H suggest that the concentrations of the four cytokines in the H5N1 treatment group are higher than those in the mutant strain treatment group and the (miR-HA-3p blocker+H5N1) treatment group. This is consistent with the cytokine detection results in the previous macrophages model.

Figure 7:
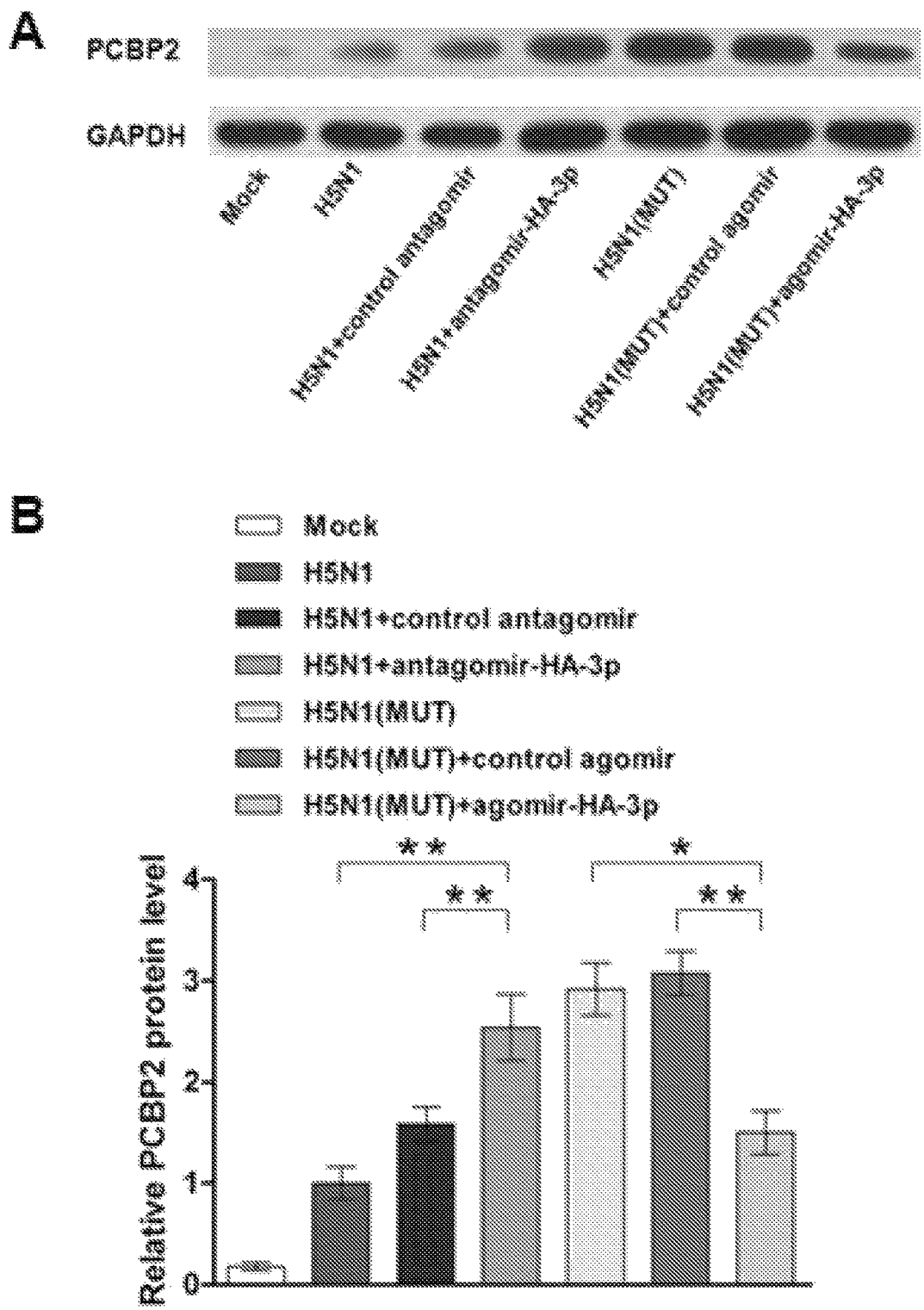
FIG. 7 shows the PCBP2 protein levels in the lungs of the mice under different treatment conditions after four days.

3). FIG. 7 shows the PCBP2 protein levels in the lungs of the mice under different treatment conditions after four days. The result of FIG. 7 shows that, after 4 days, the PCBP2 protein content in lungs of the mice in the H5N1 treatment group is significantly lower than that of the mice in the (H5N1+miR-HA-3p blocker) treatment group and in the H5N1 (MUT) treatment group.

Figure 8:
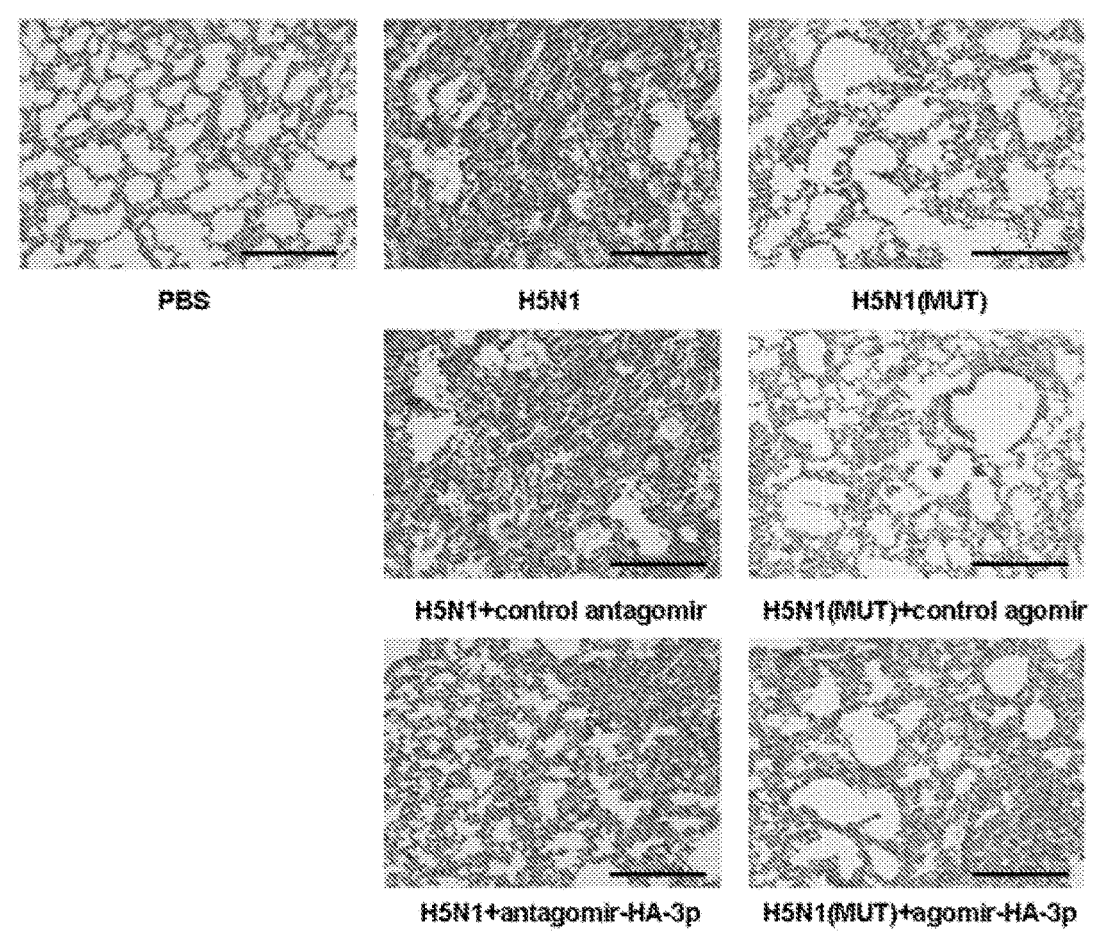

4). FIG. 8 shows the research results of the lung tissues of multiple groups of laboratory mice by histopathological method. The detection result of FIG. 8 shows that blocking miR-HA-3p can relieve the inflammatory injury in the lungs of mice. The mice in the H5N1 treatment group experience severe necrosis of bronchial epithelial cells accompanied with inflammatory reaction. On the contrary, the mice in the (miR-HA-3p blocker+H5N1) treatment group and in the H5N1(MUT) treatment group have moderate inflammatory reactions four days after infection.

The above experimental result suggests that using the miR-HA-3p blocker to block the binding of miR-HA-3p with the target mRNA can decrease the death rate of the mice infected with H5N1 and slow down the weight loss rate of mice. This conclusion has also been confirmed in the H5N1 (MUT) treatment group.

Conclusions:

The experiments results of the present invention demonstrate that, after infecting host cells, the H5N1 will release a special small molecule miR-HA-3p that will enter the in vivo circulation of host, and the expression level of miR-HA-3p is in direct correlation with the viral infection degree.

Furthermore, the target gene of miR-HA-3p is PCBP2, and miR-HA-3p acts on the PCBP2 mRNA to down-regulate the PCBP2 protein expression, resulting in enhanced MAV-mediated anti-virus process, so as to cause an overactive immune response or a cytokine storm during the H5N1 invasion.

Blocking miR-HA-3p can achieve the purpose of regulating the expression level of miR-HA-3p, which can thus relieve and treat a variety of immune responses and histological lesions induced by the H5N1 virus, and achieve new scientific and technological breakthroughs on the basis of the current research on H5N1, even bring the theoretical research of H5N1 to a new level.

The present invention creatively introduces microRNA therapy to the treatment of H5N1, and confirms the presence of H5N1-specific miRNA with a series of original test methods, such as prediction and identification of microRNA, macrophage tests, and mouse model tests. This therapy has strong specificity, high efficiency, less side effects and low cost, and the present invention has very broad application prospects owing to the innovation on method.

On this basis, the present invention also confirms that this specific miRNA precursor exists in multiple H5N1 virus isolated strains, suggesting that such miRNA may also be stably present in H5N1 virus variants, and the existing vaccines can only achieve the purpose of preventing H5N1; however, H5N1 virus mutates quickly, with which the speed of vaccine development is unable to match. In the present invention, the method for the targeted therapy of H5N1 virus-induced diseases using miR-HA-3p blockers is an innovative approach to provide new ideas and new methods for human to resist the H5N1 virus and its variants.

Example 5 Application of Avian Influenza Virus or the miRNA Thereof

The miRNA of the present invention is used for: (a) the preparation of a reagent, a detecting chip or a kit to detect avian influenza; (b) the preparation of a regulator to regulate the PCBP2 expression or activity; and (c) the preparation of reagents to regulate the expression of cytokines.

The nucleic acid chip to detect avian influenza virus or avian influenza comprises: a solid-phase carrier; and oligonucleotide probes orderly fixed on said solid-phase carrier, said oligonucleotide probe specifically capturing the miRNA of the present invention.

The nucleic acid chip to detect avian influenza virus or avian influenza of the present invention can screen miRNA probes in a high-throughput way that stably change in serum, and furthermore predict and diagnose diseases through the overall change of miRNA in serum. Firstly types of miRNAs that have no less than one copy in serum are determined by the sequencing or quantitative PCR method, then reverse complementary probes of these miRNAs are synthesized, and then these probes are spotted on a 75×25 mm chemically modified glass slide by a chip spotter SmartArray™. The samples spotted to the chip further include U6 as an interior label, tRNA, an artificially prepared external label with 30-base length, a positive control Hex, etc. The whole dot array is divided into four sub-arrays, each of which has 23 rows and 21 columns, with dot interval of 185 μm and dot diameter of about 130 μm, and each probe is replicated three times.

The chip operation process is as follows: (1) extraction of total RNA from serum/plasma, and detection of the mass of total RNA by formaldehyde denaturing gel electrophoresis; (2) isolation of miRNA: taking 50-100 μg of total RNA, and isolating miRNA with Ambion's miRNA Isolation Kit (Cat #. 1560); (3) fluorescence labelling of miRNA samples: performing fluorescence labelling with T4 RNA ligase labelling method, then precipitating with absolute ethyl alcohol, and blow-drying for chip hybridization; (4) hybridization and washing: dissolving the RNA in a 16 μL hybridization solution (15% formamide; 0.2% SDS; 3×SSC; and 50×Denhardt's solution), and hybridizing overnight at 42° C., and after hybridization, washing in a liquid containing 0.2% SDS and 2×SSC at about 42° C. for 4 minutes, then washing in 0.2×SSC at room temperature for 4 minutes, and drying the glass slide for scanning; (5) chip scanning: scanning the chip using a LuxScan 10K/A dual-channel laser scanner; and (6) data extraction and analysis: analyzing the chip image using a LuxScan 3.0 image analysis software, converting the image signals into digital signals, and finally choosing differentially expressed genes by SAM analysis.

Probes of serum/plasma miRNAs that show large expression differences between avian influenza virus infections and under the normal physiological state, which are verified with both quantitative PCR technology and biochip technology, e.g., miR-HA-3p, can be used for the preparation of biochips, and the method is the same as above. Compared with traditional chips, this chip features no significant improvement on the manufacture process and operation procedure, but it simplifies the probe library, which will greatly reduce the production cost and production time and can be easily prepared. Its specificity and practicability are also increased. Being put into practice, it can detect diseases at an early stage and guide the diagnosis and treatment, which needs no other tissue than the patient's serum/plasma.

In addition, the nucleic acid chip of the present invention is used to prepare a kit to detect avian influenza virus or avian influenza. The kit to detect avian influenza virus or avian influenza contains the nucleic acid chip of the present invention or the miRNA of the present invention.

The production process and operation procedure of the miRNA kit for the diagnosis and efficacy evaluation for avian influenza virus infections as well as the screening and efficacy evaluation of pharmaceutically active ingredients are based on quantitative and semi-quantitative PCR technology and biochip technology.

Firstly types of miRNAs that have no less than one copy in serum are determined by the sequencing or quantitative PCR method. Then the serum/plasma miRNAs that have large expression and difference degree under the diseased state and the normal physiological state, which are screened by quantitative PCR technology and biochip technology, e.g., miR-HA-3p, are determined as an indicator to predict whether an avian influenza virus infection occurs and to decide the disease phase. Finally, the number of corresponding serum/plasma miRNAs is screened, and this is the most optimized simplification of the chip probe library. This kit comprises serum/plasma miRNA primers, Taq polymerase, dNTP and other reagents. The advantage of this kit is that it needs no other tissue samples other than serum/plasma, and can detect the change trend of miRNA with the simplest probe library, and then according to this change trend the likelihood of avian influenza infection occurrence can be predicted or the pathologic stages of avian influenza infections can be diagnosed. Therefore, this kit can be put into practice to increase the possibility of detecting avian influenza virus or avian influenza at an early stage, so as to help guide diagnosis and treatment.

All the documents mentioned in the present invention are incorporatedly referred to, as well as each alone. In addition, it should be understood that after reading the teachings of the present invention described above, a skilled person in the art can make various changes or modifications of the invention, and these equivalent forms shall also fall into the scope of the present application as defined by the appended claims.

The invention claimed is:

1. A chemically modified single stranded small RNA, which is a complementary miRNA and is completely complementary to a nucleotide sequence selected from the group consisting of SEQ ID NOs: 1, 2, 3 and 4, wherein the chemically modified single stranded small RNA is an antagomir, and the chemically modified single stranded small RNA is a blocker for suppressing the miRNA whose nucleotide sequence is selected from the group consisting of SEQ ID NOs: 1, 2, and 3.

2. An artificially constructed precursor miRNA, which can be cut and expressed in an animal cell into the chemically modified single stranded small RNA of claim 1.

3. A method for down-regulating expression of a cytokine, which comprises a step of contacting a mammalian cell with the chemically modified single stranded small RNA of claim 1, wherein the cytokine is selected from the group consisting of TNFα, IFN-β, IL-6, and IL-1β.

4. A method for up-regulating expression of PCBP2, comprising contacting a mammalian cell with the chemically modified single stranded small RNA of claim 1 to upregulate the expression of PCBP2.

* * * * *